US008980179B2

(12) United States Patent
Geddes

(10) Patent No.: US 8,980,179 B2
(45) Date of Patent: Mar. 17, 2015

(54) ANGULAR-DEPENDENT METAL-ENHANCED FLUORESCENCE

(75) Inventor: Chris D. Geddes, Bel-Air, MD (US)

(73) Assignee: University of Maryland, Baltimore County, Baltimore, MD (US)

(*) Notice: Subject to any disclaimer, the term of this patent is extended or adjusted under 35 U.S.C. 154(b) by 521 days.

(21) Appl. No.: 11/750,119

(22) Filed: May 17, 2007

(65) Prior Publication Data
US 2007/0269826 A1 Nov. 22, 2007

Related U.S. Application Data

(60) Provisional application No. 60/747,465, filed on May 17, 2006.

(51) Int. Cl.
G01N 33/53 (2006.01)
G01N 33/553 (2006.01)
G01N 33/58 (2006.01)
G01N 21/552 (2014.01)
G01N 21/25 (2006.01)
G01N 21/65 (2006.01)

(52) U.S. Cl.
CPC .......... *G01N 33/553* (2013.01); *G01N 21/554* (2013.01); *G01N 2021/258* (2013.01); *G01N 21/658* (2013.01); *G01N 33/582* (2013.01); Y10S 977/924 (2013.01)
USPC ..................................... 422/82.02; 977/924

(58) Field of Classification Search
CPC .......... G01N 2021/258; G01N 21/554; G01N 21/658
USPC ..................................... 422/82.08; 977/924
See application file for complete search history.

(56) References Cited

U.S. PATENT DOCUMENTS

| 5,017,009 | A | 5/1991 | Schutt et al. |
| 5,449,918 | A | 9/1995 | Krull et al. |
| 5,866,433 | A | 2/1999 | Schalkhammer et al. |
| 6,180,415 | B1* | 1/2001 | Schultz et al. ............ 436/518 |
| 6,485,962 | B1* | 11/2002 | Tabacco et al. ........... 435/288.7 |
| 6,579,726 | B1* | 6/2003 | Natan et al. .............. 436/518 |
| 7,095,502 | B2 | 8/2006 | Lakowicz et al. |
| 7,253,452 | B2 | 8/2007 | Steckel et al. |
| 7,348,182 | B2 | 3/2008 | Martin et al. |

(Continued)

FOREIGN PATENT DOCUMENTS

| WO | 89/09408 | 10/1989 |
| WO | WO2004/024191 | 3/2004 |

(Continued)

OTHER PUBLICATIONS

Aslan K, Gryczynski I, Malicka J, Lakowicz JR, Geddes CD (2005) Metal-enhanced fluorescence: An emerging tool in biotechnology. *Curr Opin Biotechnol* 16(1):55-62.

(Continued)

*Primary Examiner* — Paul Hyun
(74) *Attorney, Agent, or Firm* — Marianne Fuierer; Moore & Van Allen, PLLC

(57) ABSTRACT

The present invention relates to detection of fluorescence, and more particularly, to the use of fluorescent moieties in proximity to metallic surfaces to change the spatial distribution of fluorescence in an angular dependent manner and detecting emissions at a determined optimal detection angle thereby increasing sensitivity of the detection.

9 Claims, 23 Drawing Sheets

(56) References Cited

U.S. PATENT DOCUMENTS

| | | | |
|---|---|---|---|
| 7,351,590 | B2 | 4/2008 | Martin |
| 7,648,834 | B2 | 1/2010 | Moore |
| 7,718,445 | B2 | 5/2010 | Martin |
| 2003/0228682 | A1 | 12/2003 | Lakowicz et al. |
| 2004/0039158 | A1 | 2/2004 | Lakowicz et al. |
| 2005/0042615 | A1* | 2/2005 | Smith et al. ............... 435/6 |
| 2005/0053974 | A1* | 3/2005 | Lakowicz et al. .......... 435/6 |
| 2005/0142605 | A1* | 6/2005 | Malak ........................ 435/6 |
| 2005/0202464 | A1 | 9/2005 | Lakowicz et al. |
| 2006/0147927 | A1 | 7/2006 | Geddes et al. |
| 2006/0256331 | A1 | 11/2006 | Lakowicz et al. |

FOREIGN PATENT DOCUMENTS

| | | |
|---|---|---|
| WO | WO2004/059279 | 7/2004 |
| WO | WO2006/052548 | 5/2006 |
| WO | WO2006/074130 | 7/2006 |
| WO | WO2006/137945 | 12/2006 |
| WO | WO2006/138698 | 12/2006 |
| WO | WO2007/053210 | 5/2007 |

OTHER PUBLICATIONS

Aslan K, Holley P, Geddes CD (2006) Microwave-accelerated metal enhanced fluorescence (MAMEF) with silver colloids in 96-well plates: Application to ultra fast and sensitive immunoassays, High Throughput Screening and drug discovery. *J Immunol Methods* 312:137-147.

Aslan K, Geddes CD (2006) Microwave accelerated and metal enhanced fluorescence myoglobin detection on silvered surfaces: Potential application to myocardial infarction diagnosis. *Plasmonics* 1(1):53-59.

Malicka J, Gryczynski I, Geddes CD, Lakowicz JR (2003) Metal-enhanced emission from indocyanine green: A new approach to in vivo imaging. *J Biomed Opt* 8(3):472-478.

Geddes CD, Cao H, Gryczynski I, Grcyznski Z, Fang J, Lakowicz JR (2003) Metal-enhanced fluorescence (MEF) due to silver colloids on a planar surface: Potential applications of indocyanine green to in vivo imaging. *J Phys Chem A* 107(18):3443-3449.

Aslan K, Leonenko Z, Lakowicz JR, Geddes CD (2005) Fast and slow deposition of silver nanorods on planar surfaces: Application to metal-enhanced fluorescence. *J Phys Chem B* 107(13):6247-6251.

Aslan K, Leonenko Z, Lakowicz JR, Geddes CD (2005) Rapid deposition of triangular silver nanoplates on planar surfaces: Application to metal-enhanced fluorescence. *J Phys Chem B* 109(8):3157-3162.

Parfenov A, Gryczynski I, Malicka J, Geddes CD, Lakowicz JR (2003) Enhanced fluorescence from fluorophores on fractal silver surfaces. *J Phys Chem B* 107:8829-8833.

Geddes CD Parfenov A,, Lakowicz JR (2003) Photodeposition of silver can result in metal-enhanced fluorescence. *Appl Spectrosc* 57(5):526-531.

Geddes CD, Parfenov A, Roll D, Fang J, Lakowicz JR (2003) Electrochemical and laser deposition of silver for use in metal-enhanced fluorescence. *Langmuir* 19(15):6236-6241.

Aslan K, Badugu R, Geddes D (2005) Metal-enhanced fluorescence from plastic substrates. *J Fluoresc* 15(2):99-104.

Geddes CD, Parfenov A, Roll D, Gryczynski I, Malicka J, Lakowicz JR (2004) *Spectrochimica Acta Part A* 60(8-9):1977-1983.

Aslan K, Leonenko Z, Lakowicz JR, Geddes CD (2005) Annealed silver-island films for applications in metal-enhanced fluorescence: Interpretation in terms of radiating plasmons. *J Fluoresc* 15(5):643-654.

Aslan K, Perez-Luna VH (2004) Quenched emission of fluorescence by ligand functionalized gold nanoparticles. *J Fluoresc* 14:401-405.

Dulkeith E, Morteani AC, Niedereichholz T, Klar TA, Feldmann J, Levi SA, van Veggel FCJM, Reinhoudt DN, Moller M, Gittins DI (2002) Fluorescence quenching of dye molecules near gold nanoparticles: Radiative and nonradiative effects. *Phys Rev Lett* 89:203002.

Dulkeith E, Ringler M, Klar TA, Feldmann J, Javier AM, Parak WJ (2005) Gold nanoparticles quench fluorescence by phase induced radiative rate suppression. *Nano Lett* 5(4):585-589.

Yguerabide J, Yguerabide E (1998) Light-scattering submicroscopic particles as highly fluorescent analogs and their use as tracer labels in clinical and biological applications—I. *Theor Anal Biochem* 262:137-156.

Yguerabide J, Yguerabide E (1998) Light-scattering submicroscopic particles as highly fluorescent analogs and their use as tracer labels in clinical and biological applications—II. Experimental characterization. *Anal Biochem* 262:157-176.

Aslan K, Holley P, Davies L, Lakowicz JR, Geddes CD (2005) Angular-ratiometric plasmon-resonance based light scattering for bioaffinity sensing. *J Am Chem Soc* 127:12115-12121.

Mie G (1908) *Ann Phys* 25:377-445.

Lakowicz JR (2001) Radiative decay engineering: biophysical and biomedical applications. *Anal Biochem* 298;1-24.

Lakowicz JR (2005) Radiative decay engineering 5: Metal-enhanced fluorescence and plasmon emission. *Anal Biochem* 337:171-194.

Liebermann T, Knoll W (2000) Surface-plasmon field-enhanced fluorescence spectroscopy colloids and surfaces. A: *Physicochemical and Eng Aspects* 171:115-130.

Lakowicz JR (2004) Radiative decay engineering 3. Surface plasmon-coupled directional emission. *Anal Biochem* 324:153-169.

Makarava N., Parfenov, Baskakov, (2005) water—soulble Hybrid Nanoclusters with Extra Bright and Photostable Emissions: A new tool for Biological Imaging. Biophysical Journal vol. 89, pp. 572-580.

Aslan K, Gryczynski I, Malicka J, Lakowicz JR, Geddes CD (2005) In: Shayne G (ed) Drug discovery handbook. Wiley, New Jersey, pp. 603-666.

Geddes CD, Aslan K, Gryczynski I, Malicka J, Lakowicz JR (2004) In: Geddes CD Lakowicz JR (eds) Reviews in Fluorescence 2004. Kluwer Academic/Plenum Publishers, New York, pp. 365-401.

Geddes CD, Aslan K, Gryczynski I, Malicka J, Lakowicz JR (2005) Radiative decay engineering. In: Geddes CD, Lakowicz JR (eds) Topics in fluorescence spectroscopy. Kluwer Academic/Plenum Publishers, New York, pp. 401-448.

* cited by examiner

FITC-HSA on Glass
Em: 225°, Ex: 90°

FITC-HSA on
200 nm Gold Colloids
Em: 225°, Ex: 90°

FITC-HSA on Glass
Em: 340°, Ex: 90°

FITC-HSA on
200 nm Gold Colloids
Em: 340°, Ex: 90°

ANGULAR-DEPENDENT METAL-ENHANCED FLUORESCENCE

CROSS-REFERENCE TO RELATED APPLICATION

The present application claims priority to U.S. Provisional Patent Application No. 60/747,465 filed on May 17, 2006, the contents of which are hereby incorporated by reference herein.

BACKGROUND OF THE INVENTION

1. Field of the Invention

The present invention relates to detection assays, and more particularly, to the use of fluorescent moieties in proximity to metallic surfaces to change the spatial distribution of fluorescence in an angular dependent manner thereby increasing sensitivity of the assay.

2. Background of the Related Art

Over the past 10 years, fluorescence has become a dominant technology in medical testing, drug discovery, biotechnology and cellular imaging. The use of fluorescence technology has greatly enhanced the ability to detect specific molecules leading to rapid advancements in diagnostics. For example, fluorescence detection is widely used in medical testing and glucose analysis because of the high degree of sensitivity obtained using fluorescent techniques. Small numbers of molecules can be detected using fluorescence technology.

Metal-Enhanced Fluorescence (MEF), a phenomenon where the quantum yield and photostability of weakly fluorescing species are dramatically increased, due to proximity to free-electron rich metals, is becoming a powerful tool for the fluorescence-based applications of drug discovery [1, 2] high-throughput screening [3, 4] immunoassays [5] and protein-protein detection [1, 4, 6].

In this regard, many surfaces have been developed for metal-enhanced fluorescence [1-5], primarily based on silver nanoparticles, such as those comprised of silver islands [1, 5, 7], silver colloids [8], silver nano-triangles [9], silver nano-rods [10] and even fractal-like silvered surfaces [11]. Several modes of silver deposition have also been developed, such as by wet chemistry [1, 9, 10], deposition by light [12] and electrochemically [13], on glass [5] and plastic substrates [14], HTS wells [3] and even electrodes [15].

However, fluorescence is normally an isotropic process, which means that when a fluorophore is excited, its fluorescence emission radiates in 360°, with an equal intensity at all angles. Thus, nearly all fluorescence is lost in many analytical and clinical applications of fluorescence because the detection measurement occurs over just a few degrees. For example, a fluorescence fluorometer, works by exciting a solution of fluorophores and measuring the fluorescence emission at 90° to the excitation light. In these measurements, only 1-5% of light, at the very best, is observed, meaning that >95% of the total light available is lost.

Providing a system and method that has the capability of capturing this light, would significantly increase detection limits in the many applications of fluorescence, such as in bio-assays and even imaging histology. Thus, there is a need for a biosensor platform and system that overcomes the shortcomings of the prior art and provides for increased sensitivity and signal production.

SUMMARY OF THE INVENTION

The present invention relates to the use of metallic nanoparticles that generate non-isotropic, angular dependent fluorescence emission for increasing sensitivity of detection methods.

The present invention relates to a method of detecting fluorescence emission using plasmonic emissions from metallic surfaces in combination with induced fluorescence emissions, wherein the plasmonic emissions emitted from metallic surfaces are combined with induced fluorescence emissions and detected at an optimal detection angle. Preferably, depending on the size and shape of the metallic surface, the optimal angle for detecting intensity of emitted emissions is predetermined, thereby increasing the sensitivity of the assay for lower concentrations of target substance.

In one aspect, the present invention relates to a method for enhancing emission from a fluorescence molecule, the method comprising:
- positioning the fluorescence molecule near a metallic structure immobilized on a surface;
- irradiating the fluorescence molecule with a radiation source at an excitation angle in an amount sufficient to cause non-raditative transfer of energy from the fluorescence molecule to plasmons on the metallic structure;
- detecting emissions from fluorescence molecule in combination with plasmonic emissions at an angle different from that of the excitation angle.

In another aspect, the present invention relates to a bioassay for measuring concentration of receptor-ligand binding, the method comprising:
(a) preparing metallic structures immobilized on a surface wherein the metallic structures have positioned thereon a receptor molecule having affinity for the ligand;
(b) contacting the metallic structures attached to the receptor molecule with a sample suspected of comprising the ligand of interest, wherein any ligand in the sample will bind to the receptor molecule to form a receptor-ligand complex;
(c) contacting the receptor-ligand complex with a detector molecule having affinity for the ligand to form a receptor-ligand-detector complex, wherein the detector molecule is a fluorescence label,
(d) exposing the fluorescence label to excitation electromagnetic energy at an excitation angle; and
(e) measuring the intensity of radiation emitted from excited surface plasmons of the metallic surface and fluorescence label at a detection angle, wherein the excitation angle is different from the detection angle.

Preferably, the metallic surfaces take the form of metallic islands, nanostructures, colloids, porous matrix or a continuous surface with metallic inclusions. The metallic element may include any metal that exhibits plasmonic emissions and preferably, the metallic element is a noble metal such as silver, gold, platinum, aluminum and/or copper.

In yet another aspect, the present invention relates to a method of metal-enhanced fluorescence sensing, comprising:
(a) applying a metallic material to a surface used in a detection system;
(b) introducing a solution containing at least one biomolecule for disposing near the metallic surface, wherein the biomolecule comprises a fluorescence tag;
(c) applying electromagnetic energy in an amount sufficient amount to excite fluorescence tag and surface plasmons on metallic material, wherein the electromagnetic energy is delivered at an excitation angle; and (d) measuring surface plasmonic emissions at a detection angle that is different from the excitation angle.

In another aspect, the present invention relates to a biosensing method for measuring concentration of an analyte, the method comprising:
(a) preparing metallic particles comprising a noble metal and at least partially coated with a binding component having an affinity for the analyte;
(b) contacting the binding components with the analyte that has an affinity for the binding component;
(c) contacting any bound analyte with a fluorescence tag;
(d) exposing the system comprising the metallic particles and fluorescence tag with excitation electromagnetic energy in an amount sufficient to excite the fluorescence tag, wherein the electromagnetic energy is delivered at an incident angle and at a frequency matching plasmon absorption maxima of the metallic particle; and
(e) detecting the emission from surface plasmons and/or fluorescence tag at a detection angle different from the incident angle, wherein the detection angle has been predetermined for the metallic particles.

In yet another aspect, the present invention relates to a system of detecting angular-dependent metal enhanced fluorescence, the system comprising:
(a) metallic colloids positioned on a surface or in solution, wherein the metallic colloids are communicatively connected to a fluorophore tag;
(b) a source of electromagnetic energy positioned to radiate at least the fluorophore tag at an excitation angle; and
(c) a detector positioned at a detection angle for measuring the radiation emissions from the metallic colloids coupled with emission from the fluorophore tag.

Other features and advantages of the invention will be apparent from the following detailed description, drawings and claims.

DETAILED DESCRIPTION OF THE INVENTION

It has been found that the close-proximity metallic silver islands or colloids to fluorophores can alter the radioactive decay rate and/or excitation rate of such fluorophores. Further, it has been shown that quantum yield of low quantum yield fluorophores can be increased by proximity to metallic surfaces. The enhanced excitation of fluorophores in close proximity to metallic surfaces including islands, colloids, porous and continuous surfaces can have numerous applications in the biochemical and biological applications of fluorescence because of the increased intensity of the fluorescence.

Additionally, it has been found that surface plasmons (electron oscillations on the surface of metals) are easily generated and manipulated using the appropriate metal structures, such as metal films or metallic nanostructures of the appropriate size and shape. In particular, nanostructures made from the noble metals, such as those of silver or gold, with their associated strong plasmon resonance, have generated great interest because of the induced radiative response.

Figure 14:
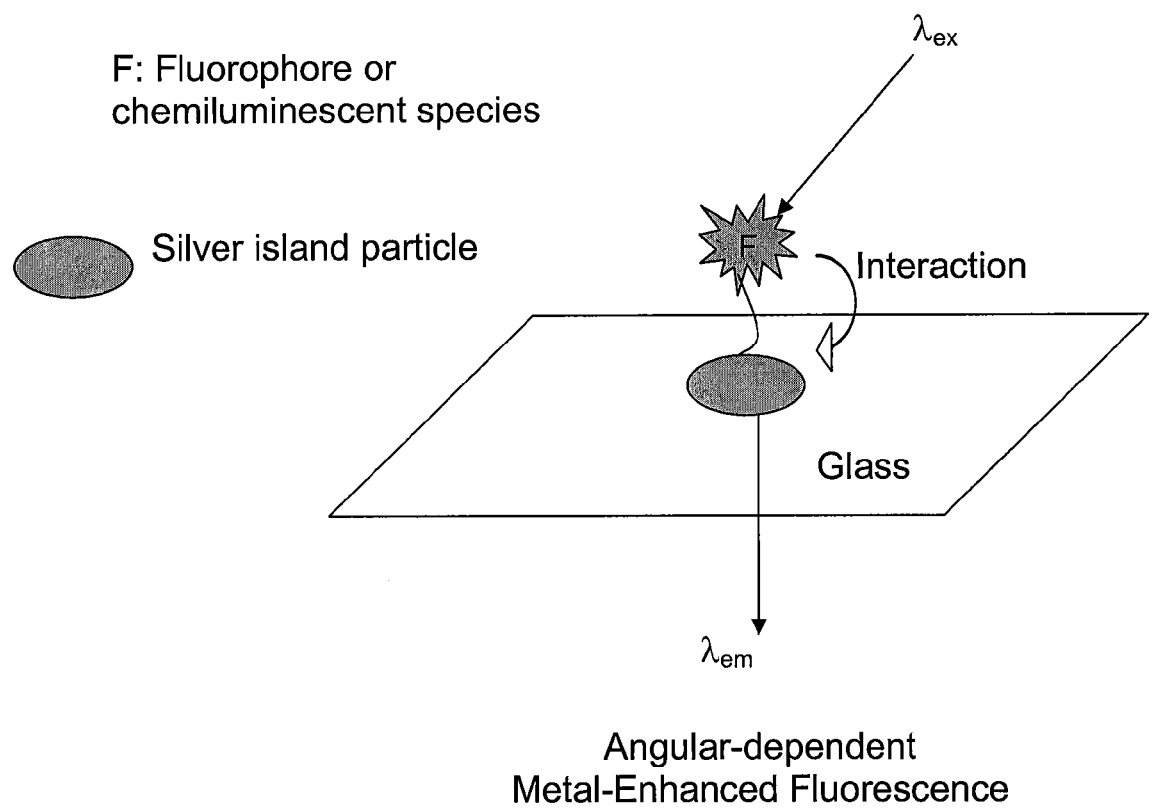
FIG. 14 shows a pictorial representation of Angular Dependent Metal-enhanced Fluorescence.
Figure 15:
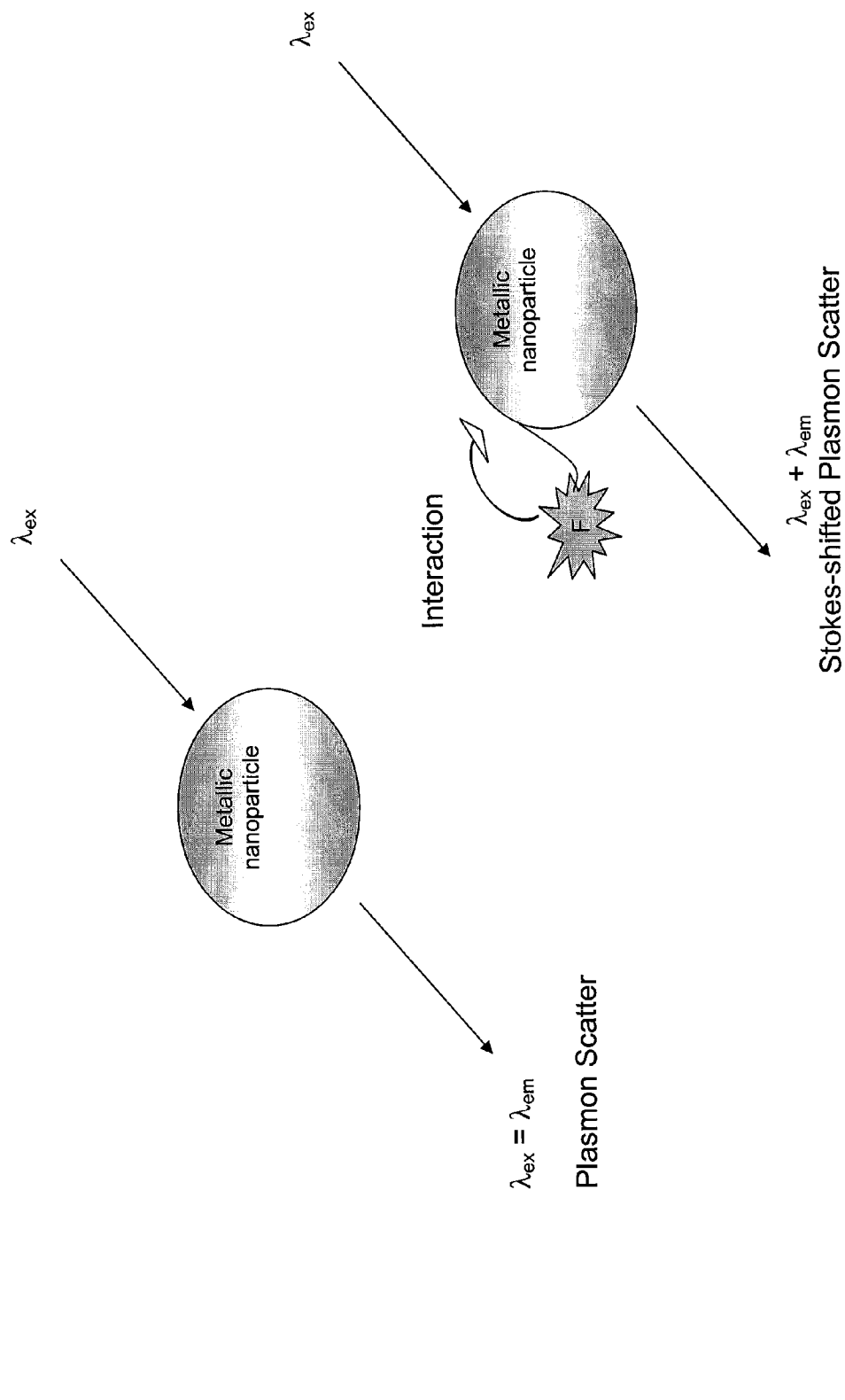
FIG. 15 shows the generation of surface plasmon emissions for solution based suspension of colloids and fluorophores.
Figure 16:
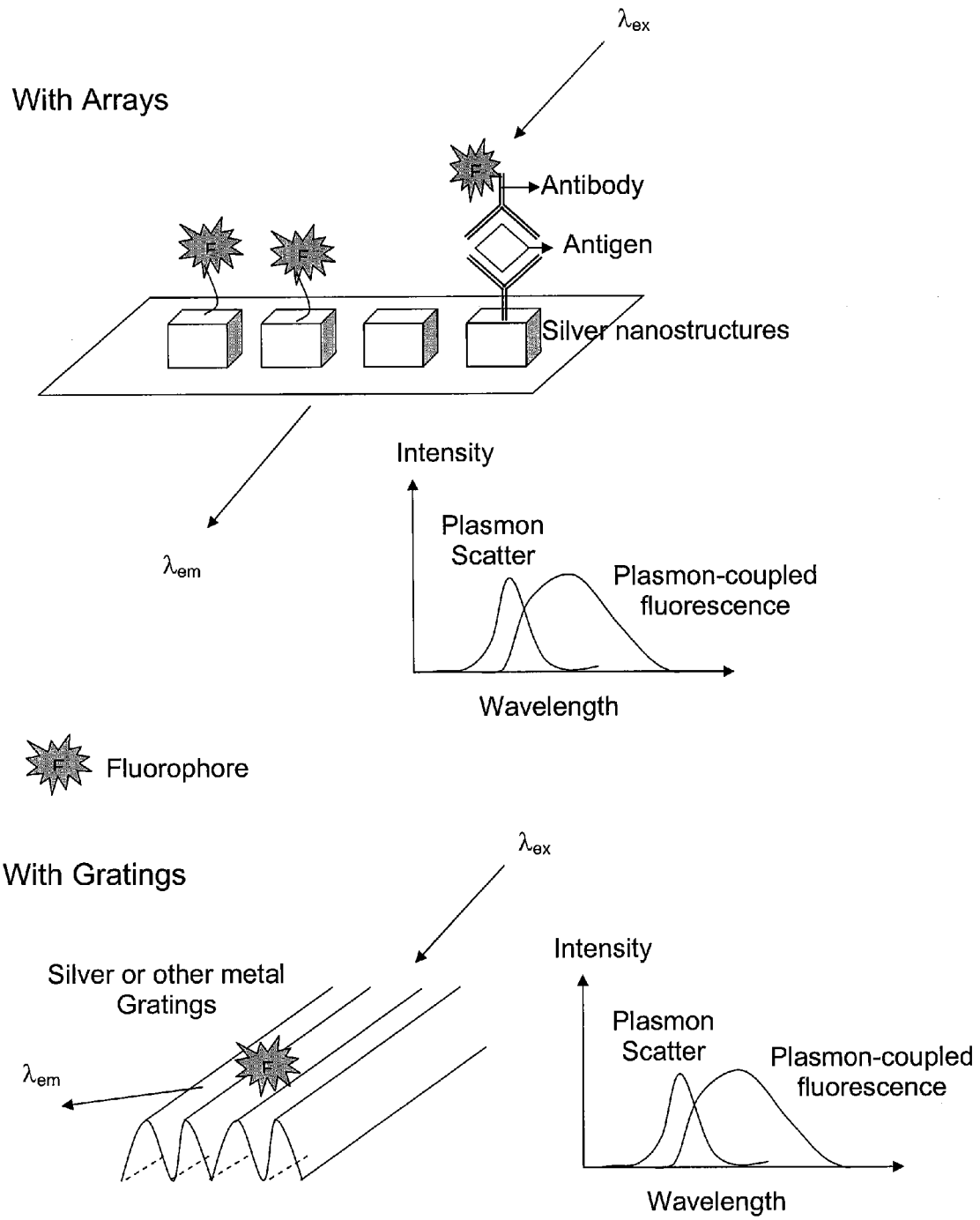
FIG. 16 shows surface DNA or protein arrays, using the present invention.

When a fluorophore is close to a metallic nanostructure, which supports surface plasmons, the fluorophore can couple its emission to the surface plasmons, the plasmons then radiating the photophysical properties of the fluorophore. The emitted plasmon controlled fluorescence is no longer isotropic, but is indeed angular dependent (i.e. different intensities at different angles), and the spatial distribution of the fluorescence follows the plasmon scattering profile of the nanostructures. This technology not only works for metallic particles on surfaces (FIG. 14), but also works for solution-based suspensions of colloids and fluorophores, (FIG. 15). In addition, different types of metallic surfaces and topographies such as an array of nanostructures or grating structures are also likely to couple emission at different angles as shown in FIG. 16.

The present invention relates to affinity biosensing using coupling of plasmon absorption and/or light scattering in metallic surfaces with fluorescing molecules. This new model system can be potentially applied to many other nanoparticle assays and has many advantages over traditional fluorescence sensing and other light-scattering approaches. For example, a single metallic nanoparticle, with the appropriate dimensions, can have the equivalent scattered intensity as $10^5$ fluorescing fluorescein molecules thereby substantially increasing detection. Further, the angular distribution of both polarized and scattered light from noble metal colloids is substantially easier to predict as compared to fluorescence.

The plasmonic scattered light from different sized colloids and density of the metal particles or nanostructures is markedly different and when coupled with the fluorescence from tag fluorophores, the optimal intensity of emissions can be detected at optimal angles relative to the incident angle.

Light sources used for applying electromagnetic energy can include any source that may apply the necessary frequency or wavelength such as arc lamps, lasers and LCD sources. Detectors can include photomultiplier tubes. Additionally, it is advantageous for the device to have a monochromator so that specific wavelengths of light may be used to excite a molecule or to detect emissions at a specific wavelength.

In one embodiment, the metallic nanostructures may be prepared by reduction of metal ions using various reducing agents, using technique known to one skilled in the art. For example, sodium hydroxide may be added to a rapidly stirred silver nitrate solution thereby forming a precipitate.

Colloids can be prepared as suspensions by citrate reduction metals. Preferred metals are silver and gold. Again, gold may be used because of the absorption of gold at shorter wavelengths. The size of the colloids and their homogeneity can be determined by the extensive publications on the optical properties of metal particles available and the effects of interface chemistry on the optical property of colloids.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

Silver island films can be formed by a chemical reduction of a silver salt on the quartz surface and that are relatively simple to fabricate. However, this approach does not provide a control of particle size, or distance of the fluorophores from the surface Enhancements of 1000 fold have been made with the realization that sample geometries have been heterogeneous and the enhancement factors spatially averaged.

The present invention provides enhanced emissions using metallized islands of elliptical, spherical, triangular or rod-like forms. In exemplary cases, the elliptical islands have aspect ratios of 3/2, and the spherical colloids have diameters of 40-200 nm. However, the invention is not limited to any particular geometry. Using known coating techniques, the placement of metallic islands could be controlled precisely, as close as 50 nm apart.

The emission enhancement may be observed at distances according to the type of fluorophore species to be detected and the type of metal. For example, emission enhancement may be observed when a fluorescence species is positioned about 4 nm to about 200 nm to metal surfaces. Preferable distances are about 5 nm to about 30 nm, and more preferably, 5 nm to about 20 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

"Fluorophore," as used herein, means any substance that emits electromagnetic energy such as light at a certain wavelength (emission wavelength) when the substance is illuminated by radiation of a different wavelength (excitation wavelength) and is intended to encompass a chemical or biochemical molecule or fragments thereof that is capable of interacting or reacting specifically with an analyte of interest in a sample to provide one or more optical signals. Additionally fluorophore includes both extrinsic and intrinsic fluorophores. Extrinsic fluorophore refer to fluorophores bound to another substance. Intrinsic fluorophores refer to substances that are fluorophores themselves. Exemplary fluorophores include but are not limited to those listed in the Molecular Probes Catalogue which is incorporated by reference herein.

Representative fluorophores include but are not limited to Alexa Fluor® 350, Dansyl Chloride (DNS-Cl), 5-(iodoacetamida)fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3,-diazol-4-yl chloride (NBD-Cl), ethidium bromide, Lucifer Yellow, 5-carboxyrhodamine 6G hydrochloride, Lissamine rhodamine B sulfonyl chloride, Texas Red™. sulfonyl chloride, BODIPY™., naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2 [(di-n-butylamino)-6 naphthyl]vinyl]pyridinium betaine (Naphtyl Styryl), 3,3'dipropylthiadicarbocyanine (diS-$C_3$-(5)), 4-(p-dipentyl aminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrirmidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

The term "biomolecule" means any carbon based molecule occurring in nature or a derivative of such a molecule. The biomolecule can be in active or inactive form. "Active form" means the biomolecule is in a form that can perform a biological function. "Inactive form" means the biomolecule must be processed either naturally or synthetically before the biomolecule can perform a biological function. Exemplary biomolecules include nucleic acids, aromatic carbon ring structures, NADH, FAD, amino acids, carbohydrates, steroids, flavins, proteins, DNA, RNA, oligonucleotides, peptide, nucleic acids, fatty acids, myoglobin, sugar groups such as glucose etc., vitamins, cofactors, purines, pyrimidines, formycin, lipids, phytochrome, phytofluor, peptides, lipids, antibodies and phycobiliproptein.

Further, it should be noted that the present invention may also use low level microwave heating of the samples to speed up biological/biochemical kinetics. Low level microwaves do not destroy or denature proteins, DNA, or RNA, but instead heat the sample sufficiently to provide for accelerated kinetics such as binding or hybridization. In addition, the microwaves are not scattered by the low density silver metal, which is contrary to most metal objects such as that recognized by placing a spoon in a microwave oven. Hence, the present invention combines the enhanced and localized signal intensities that have been reported for metals in close proximity to fluorophores with the ability to rapidly heat the samples using low level microwaves.

In one embodiment, the capture/receptor molecule is fused to a noble metal nanostructure that preferably is immobilized on a glass or polymeric smooth surface, wherein a ligand in a sample can bind to the capture/receptor molecule. A fluorescing detector biomolecule can bind to the ligand to determine the presence of such a ligand in the assay, wherein excitation of the fluorescing detector biomolecules causes the coupling of plasmonic emissions and fluorescing detector that can be detected at an optimal angle relative to the incident excitation angle.

Figure 1:
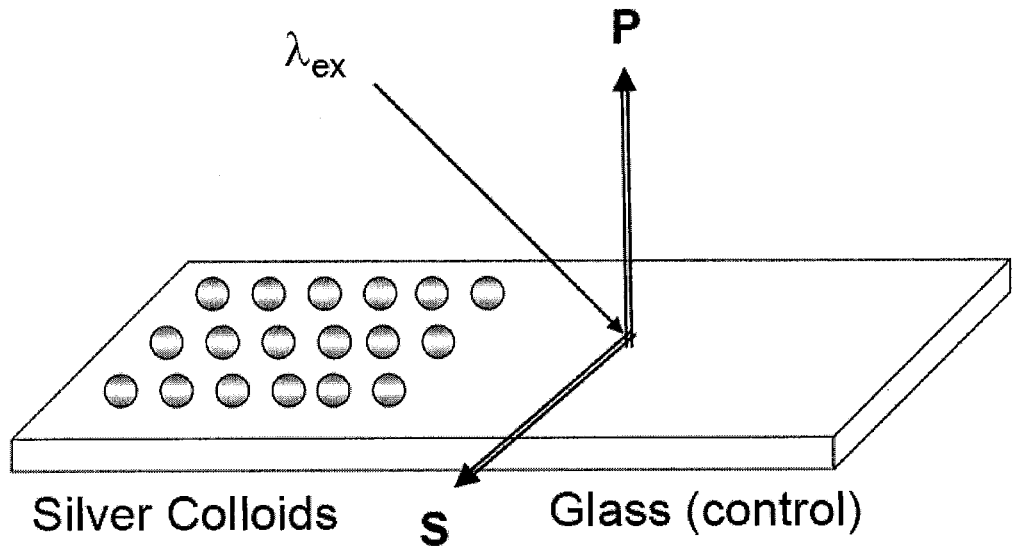
FIG. 1 shows the polarization (Top) and experimental geometry used to study angular-dependent metal-enhanced fluorescence (Bottom).
Figure 1:
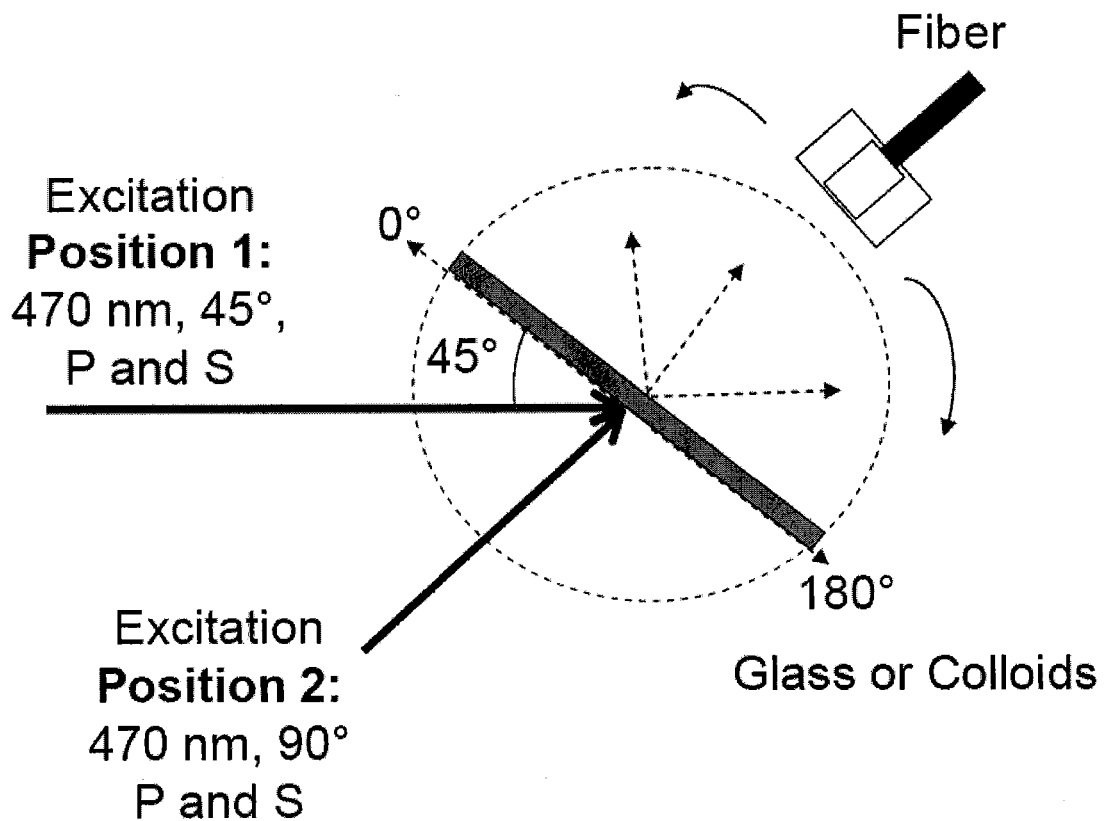

The angle-dependent polarized or scattered emissions from the metallic surfaces can be measured using using an X-Y rotating stage (Edmund Optics), modified to hold a cylindrical cuvette (a thin walled NMR tube), with a fiber optic mount, as shown in FIG. 1. The metallic structures can be illuminated with scattered or polarized laser sources with a neutral density filter being used to adjust the laser intensity. The angle-dependent light from the metallic surfaces can be collected through a dichroic sheet polarizer (Edmund optics) into a 600 micron broad wavelength fiber that was connected to an Ocean Optics HD2000 spectrofluorometer. The photostability of metallic surfaces can be measured by simply observing the polarized or scattered intensity at different angles for a specific length of time, such as 30 or 45 minutes. Preferably, the angles for measuring intensities is varied and predetermined dependent on the metal surface, shape and density of metallic particles. The electromagnetic radiation may be applied by a monochromatic laser light at a frequency similar to plasmon absorption maxima of the metallic surfaces.

The term "biological agent" means any molecule occurring in nature or a derivative of such a molecule. Exemplary biological agents may include nucleic acids, aromatic carbon ring structures, NADH, FAD, amino acids, carbohydrates, steroids, flavins, proteins, DNA, RNA, oligonucleotides, fatty acids, myoglobin, sugar groups such as glucose etc., vitamins, cofactors, purines, pyrimidines, formycin, lipids, phytochrome, phytofluor, lipids, antibodies and any type of cell.

The present invention utilizes plasmon light scattering emissions to develop the concept of angular-dependent polarization-based plasmon light scattering forbioaffinity sensing. Here, the excitation is perpendicular to the scattering plane and so no $\cos^2 \theta$ angular dependence of scatter is evident while the particles remain in the Rayleigh limit, i.e., diameter $<1/20$th $\lambda$. As particle size increase, the spatial distribution of polarized scatter around the sample changes and an increased forward scatter is observed (particles now scattering in the Mie limit), enabling large changes in polarization to be subsequently observed at angles approaching 180°, the angle of forward scatter.

The present invention employs excitation polarization perpendicular to the scattering plane, where no Rayleigh angular dependence of scattering occurs, the angular dependence due to particles scattering in the Mie limit after particle size increases, which manifests itself in a increased forward scattering, i.e., at 180°.

When a metallic nanoparticle is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength, which is often referred to as plasmon scatter. The scattering of light by very small subwavelength sized particles, is well described by Rayleigh theory. However, for larger particles, where the size of the nanoparticle is ~ greater than $1/20$ th the wavelength of light, or for Rayleigh sized particles in close proximity to one another, the scattering properties no longer obey Rayleigh theory, but indeed can be described by Mie's theory.

It is informative to briefly describe why the scattering from larger particles is no longer described by Rayleigh theory. It was previously mentioned that when a small particle is exposed to an electromagnetic field, whose wavelength is much larger than the diameter of the particle, then the electrons in the nanoparticle all sense the same phase of the incident wave, and therefore all scatter light with the same phase. In essence, the whole particle behaves as a large oscillating dipole moment, a function of the collective electron oscillations (plasmons). However, for much larger particles then the electrons on the particles can experience different phases, and therefore can oscillate with different phases. This inherently leads to interference of the light, which is scattered by the electrons from different parts of the particles. Subsequently, both the magnitude and angular distribution of the scattered light deviate from that expected of a normal oscillating electric dipole. The Mie theory for light scattering from large particles can be considered as light radiating from oscillating electric dipoles, as well as magnetic dipoles, quadruples and other higher order magnetic multipoles. Scattered light by Mie theory is well known and described by the following equation;

$$I_{scan} = \frac{2\pi}{k^2} \sum_{n=1}^{\infty} (2n+1)(|a_n|^2 + |b_n|^2)$$

where $k=2\pi n_{med}/\lambda$. One can envision the different terms in the sum as corresponding to different electric and magnetic multipoles and n is the term index. The term with n=1 corresponds to the electric dipole. The coefficients an and bn are defined in terms of the Bessel and Ricatti functions and in general are complex numbers depending on whether the refractive index of the particle is real or complex. When the particle is much smaller than the wavelength of light, the most important expression in the Mie equation becomes that of the electric dipole, and then the Mie equation reduces back to the Rayleigh expression.

The polarized-scattering from metallic surfaces can be measured using an X-Y rotating stage (Edmund Optics), that was modified to hold a cylindrical cuvette (a thin walled NMR tube), with a fiber optic mount, as shown in FIG. 1. The metallic structures can be illuminated with vertically polarized laser sources with a neutral density filter being used to adjust the laser intensity. The angle-dependent vertically polarized scattered light from the metallic surfaces can be collected through a dichroic sheet polarizer (Edmund optics) into a 600 micron broad wavelength fiber that was connected to an Ocean Optics HD2000 spectrofluorometer. The photostability aggregation of metallic surfaces can be measured by simply observing the polarized scattered intensity at different angles, such as 90 or 140 degrees for a specific length of time, such as 30 or 45 minutes.

Figure 2:
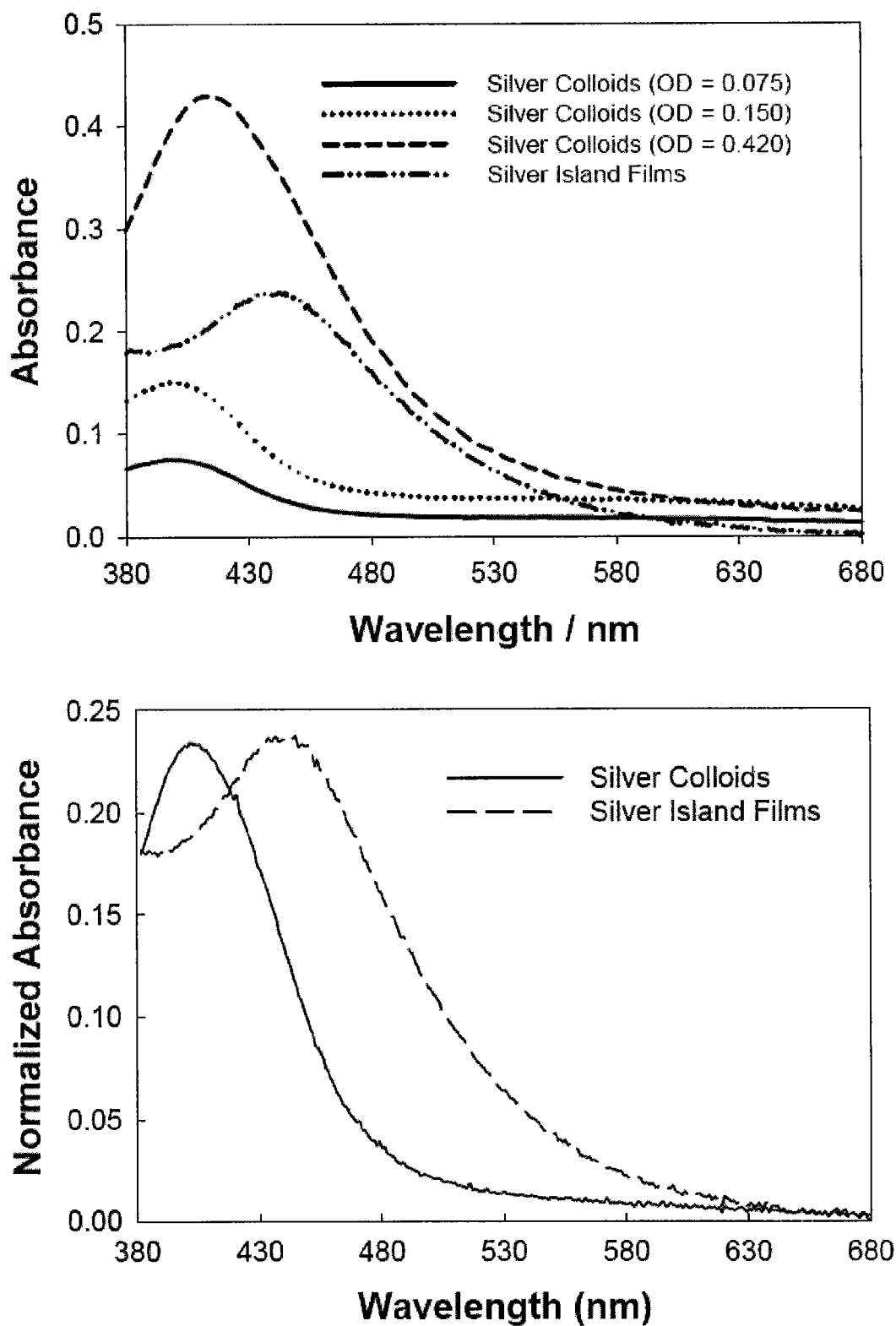
FIG. 2 shows the absorption spectra of silver colloids as a function of surface optical density (loading) (Top), and the normalized plasmon spectra of ≈20 nm silver colloids and silver island films (Bottom).

As shown in FIG. 2, absorption spectra of silver colloids increases as the surface optical density increases and silver colloids of approximately 20 nm exhibit similar absorbance at different wavelengths of excitation.

Figure 3:
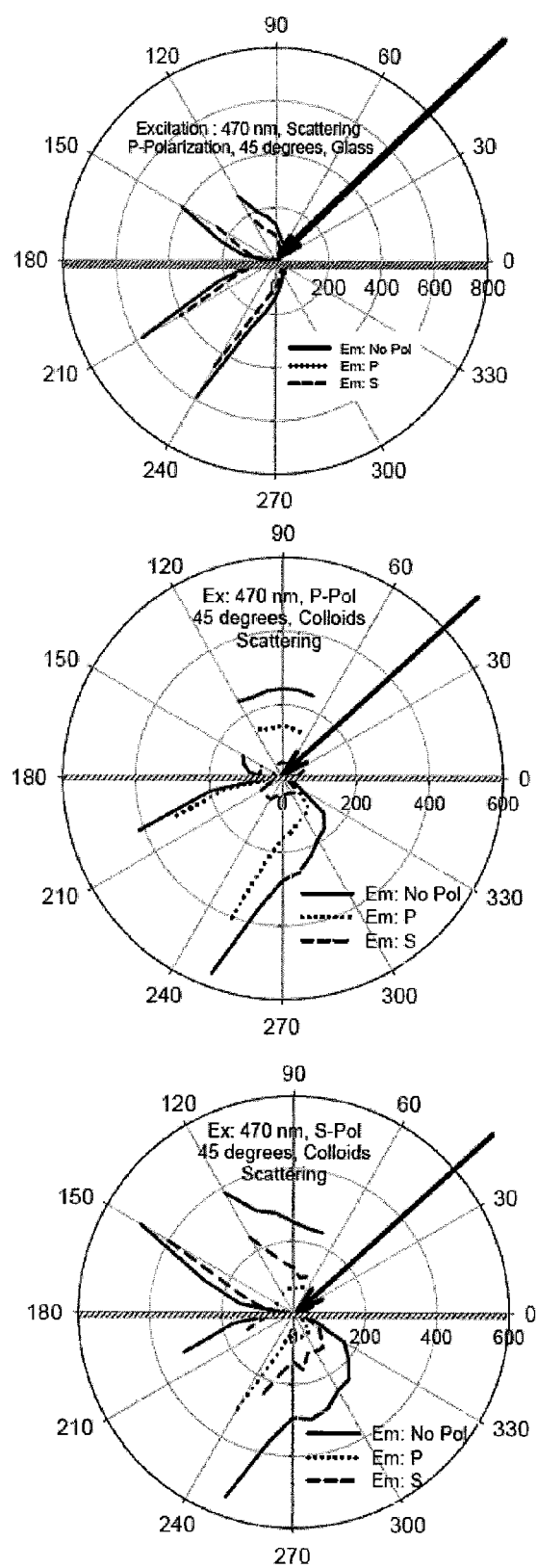
FIG. 3 shows the spatial distribution of 470 nm laser scatter from a bare glass substrate (Top) and from a colloid coated surface with an optical density of 0.075 with both P and S ex & em (Middle and Bottom respectively). ex=Excitation, em=Emission.

FIG. 3 shows the pattern of angular emissions, both polarized and scattered, from a glass surface or metallic colloid coated surface. At 470 nm excitation at a 45° angle of incident, angular detection of emissions from a glass surface can be detected at both a 90° and 180° angle relative to the angle of incident. Notably, as the colloids are added to the system, the angle range increases for detection.

Figure 4:
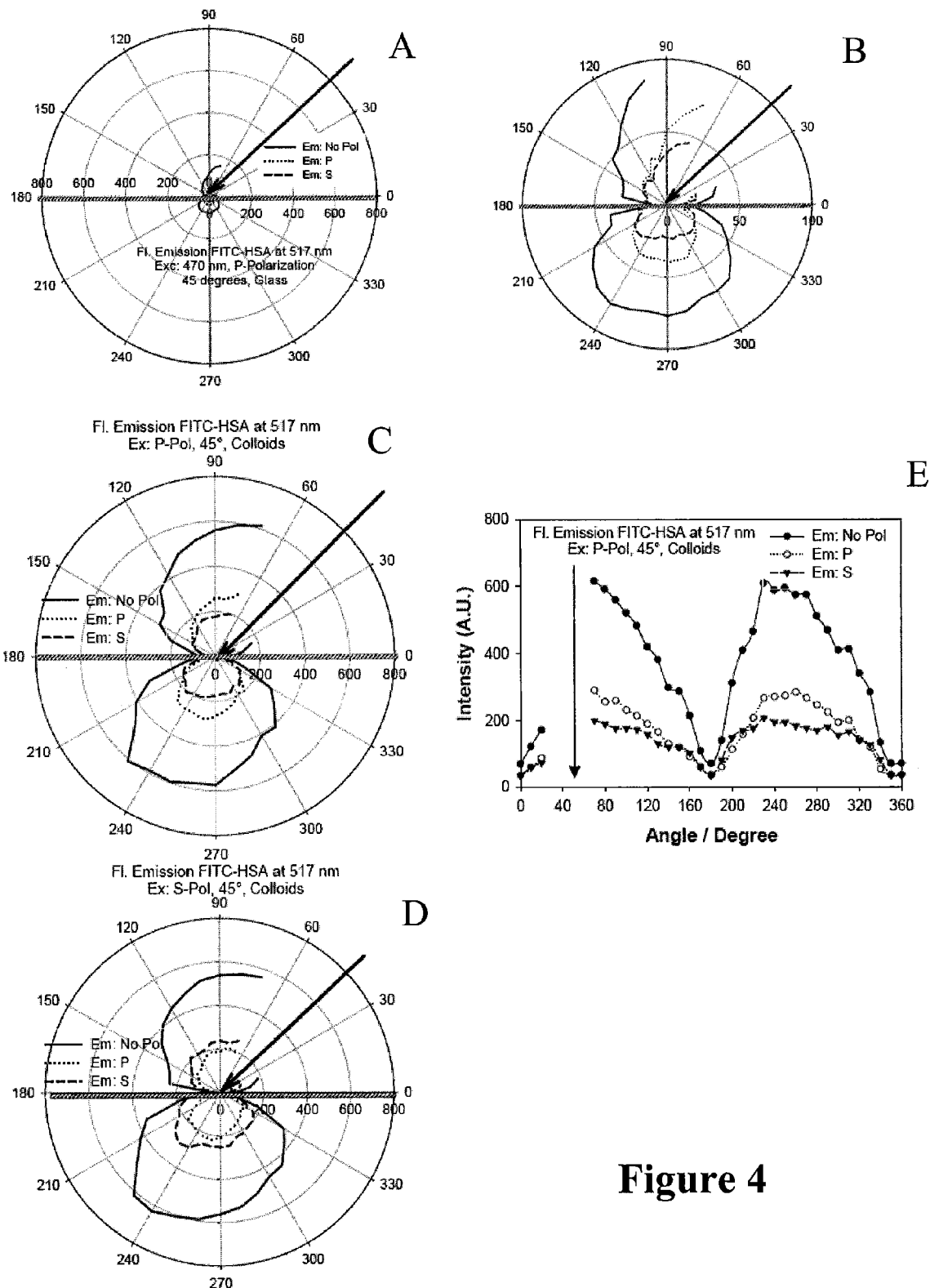
FIG. 4 shows the spatial distribution of fluorescein (FITC) emission on a bare glass substrate (A), enlarged (B), and with both P and S ex & em (C and D, respectively). (E) is a linear plot of (C). ex=excitation, em=emission.

FIG. 4 shows the intensity of p-polarization emission spectra of FITC-HSA on glass substrate and silver colloids measured to 517 nm in an angular dependent fashion over 360 degrees wherein the excitation source was positioned perpendicular to the glass substrate on the same side of the colloids and fluorophores. The emission intensity on FITC-HSA on glass and gold colloids was the lowest at the angles of 0 and 180 degrees and was the highest at about 270 degrees (at the back of the glass substrate). As shown in FIG. 4E the emission intensities were not collected at angles between 30 and 80 degrees due to the obstruction of the fiber optics holder as shown in FIG. 1. Notably on bare glass the emissions are at a minimum however, as the emissions from the metallic plasmons are coupled with the fluorophore, intensity greatly increases.

Figure 5:
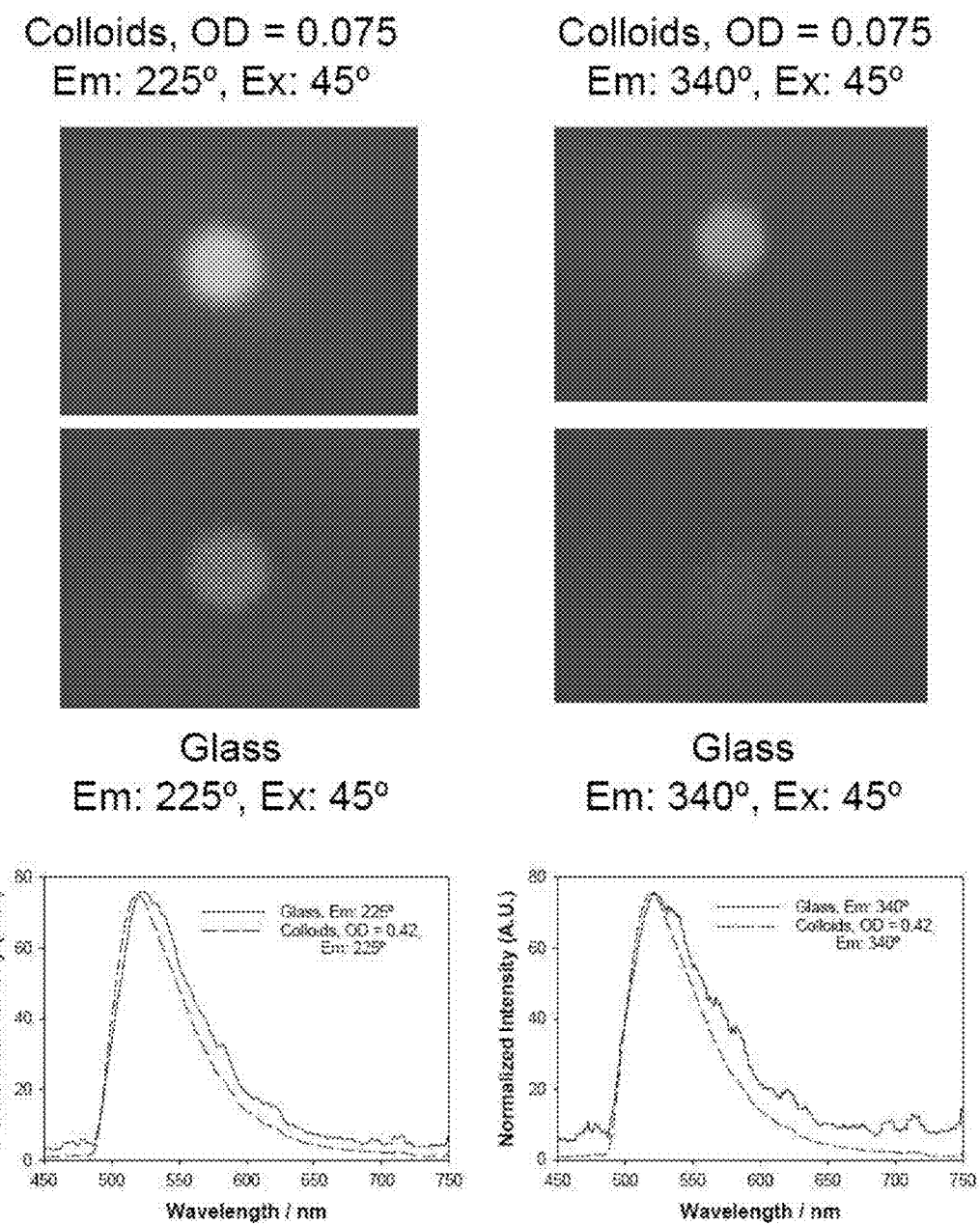
FIG. 5 shows photographs of FITC-HSA coated glass and colloid-coated glass (Top panels) and the respective normalized emission spectra at both 225 and 340 degrees (Bottom).

The photostability of FITC-HSA on silver colloids and glass was tested at two different emission angles, 225 and 340 degrees. A fluorophore conjugated to a protein within about 4 nm of the metallic surface excited the silver colloid surface plasmons in a non-radiative fashion which then scattered light. FIG. 5 shows that the emission spectrum is increased at a 225 angle relative to the 340 angle, and as such, detection at the 225 angle provides for increased sensitivity. Further the photographs of fluorescence emission show the increase in emissions with the silver colloids relative to the glass surface without plasmonic emissions. Again the angle of detection of 225 degrees provides increased intensity of emissions.

Figure 6:
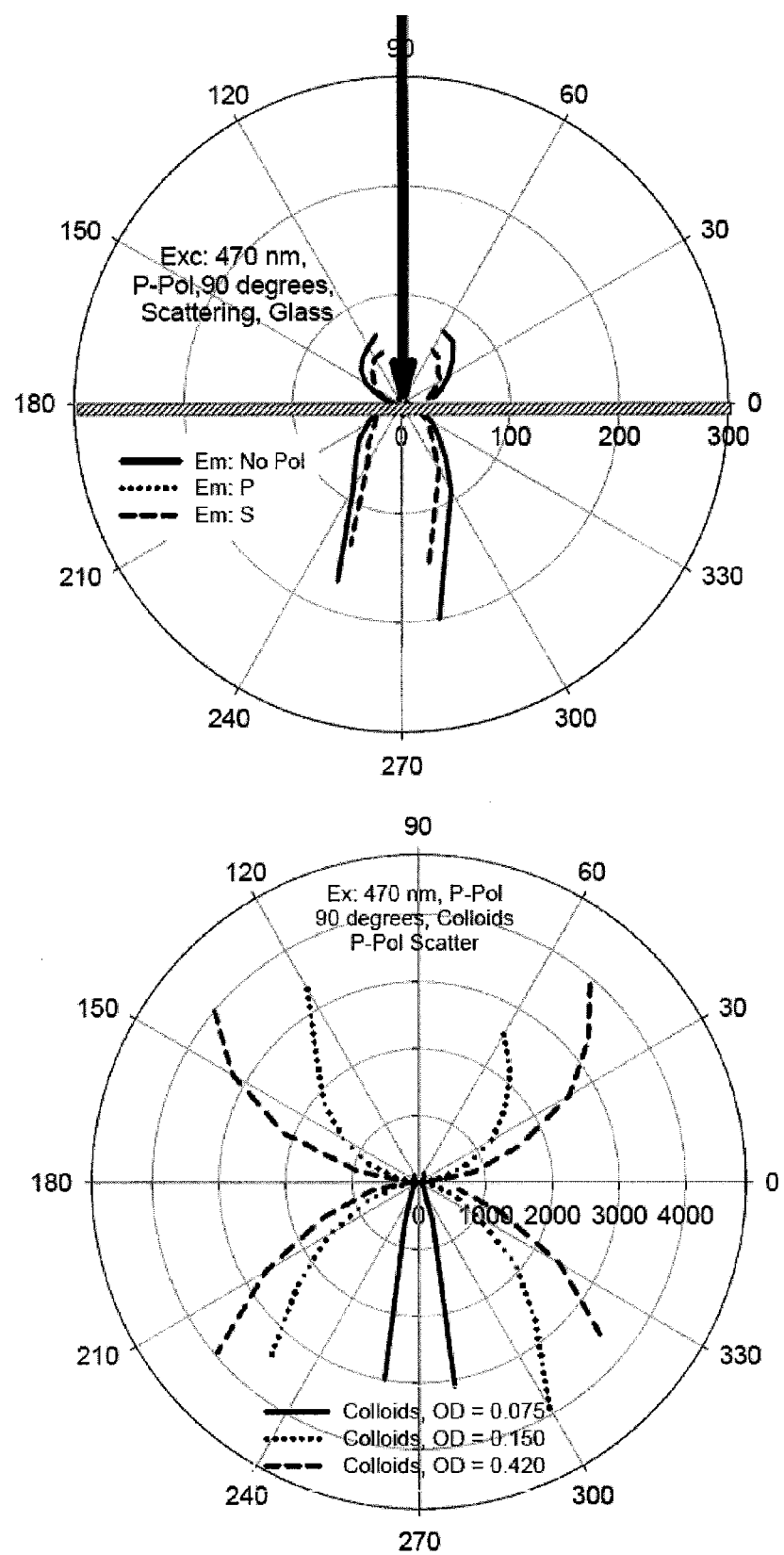
FIG. 6 shows the spatial distribution of 470 nm scatter from glass with 90 degree excitation (Top) and colloid coated glass slides of various different optical densities, surface loadings (Bottom).

FIG. 6 shows that the incident angle of excitation affects the angle of detection. Using an excitation of 470 nm wavelength, the optimal angle of detection is approximately 180 degrees from the angle of incidence. Further as the optical density on the glass surface increases, the range of detection is increased. As such, it may be beneficial to limit the optical density to limit the detection range, thereby overcoming any dilution factor that may be introduced by increasing the detection angle range and the spatial distribution of emissions.

Figure 7:
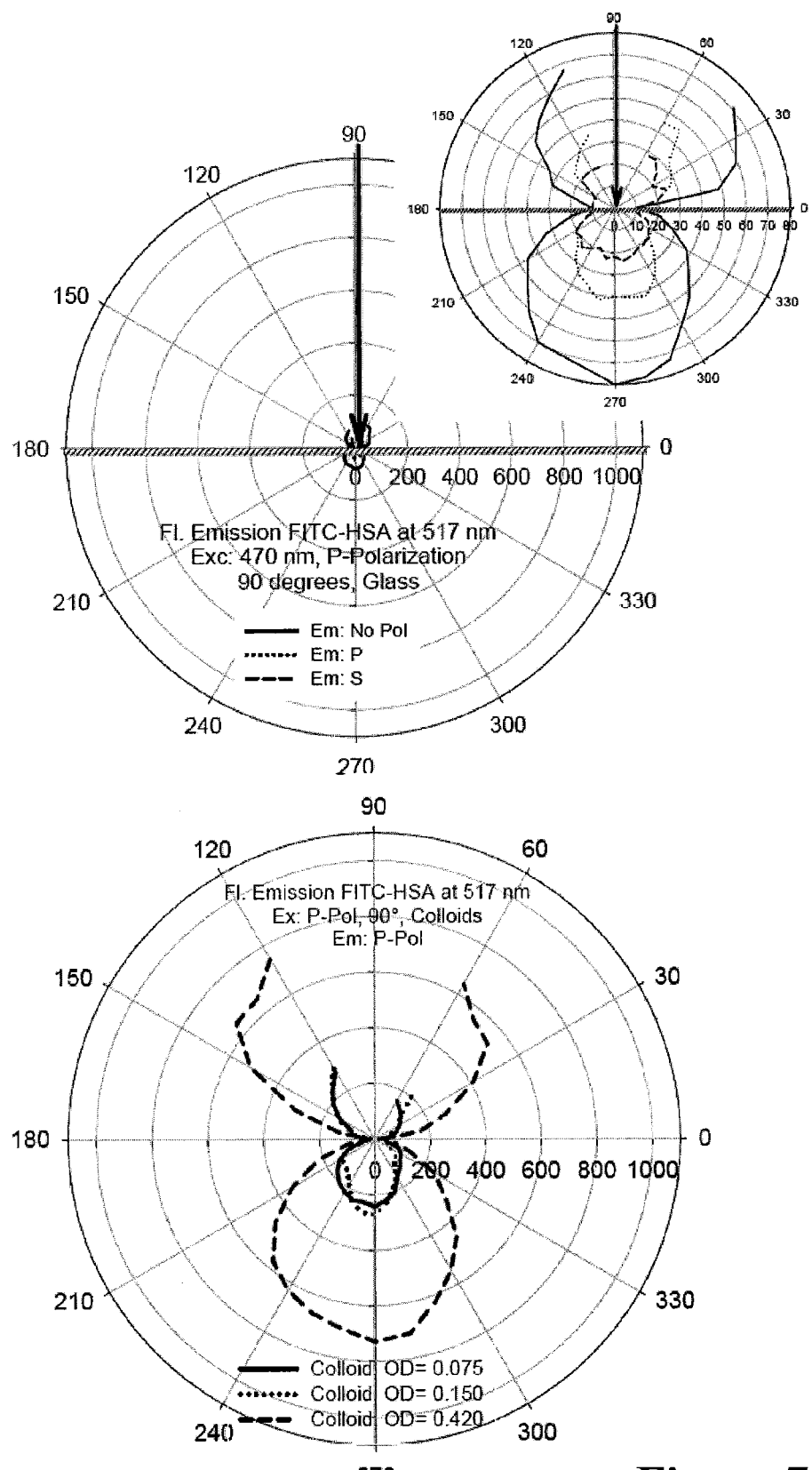
FIG. 7 shows the spatial distribution of fluorescein (FITC) emission on glass (Top), Insert-enlarged 0-80 counts per second region. Spatial distribution of fluorescein emission from colloid coated glass with various degrees of surface loading (Bottom).
Figure 8:
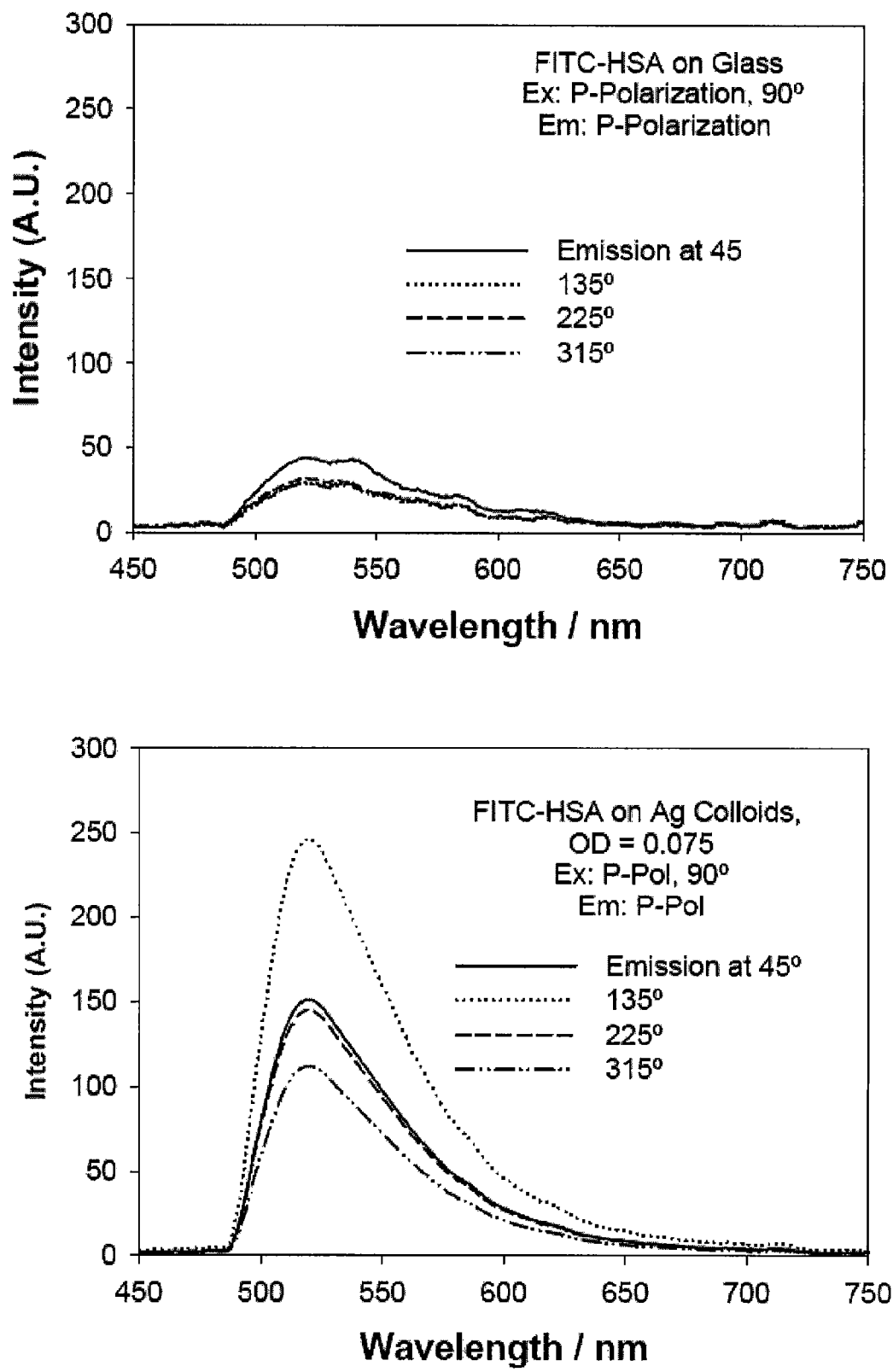
FIG. 8 shows emission spectra of FITC-HSA as a function of observation angle on both bare glass (Top) and a silver colloid coated surface (OD=0.075, Bottom)

FIG. 7 shows the spatial distribution of Fluorescein emission on glass which is almost non visible with an excitation energy of 517 nm and the spatial distribution of emission from fluorescein coupled to colloid coated glass with various degrees of surface loading. As the loading increases, the spatial distribution enlarges in the bottom figure. Notably, the excitation energy of 517 nm is not as effective as that of excitation at 470 nm FIG. 8 shows that the intensity is a function of the observation angle. Clearly, the optimal angle for detection for emissions from Ag colloids with an optical density of 0.075 with an incident angle of 90 degrees is at 135 degrees.

Figure 9:
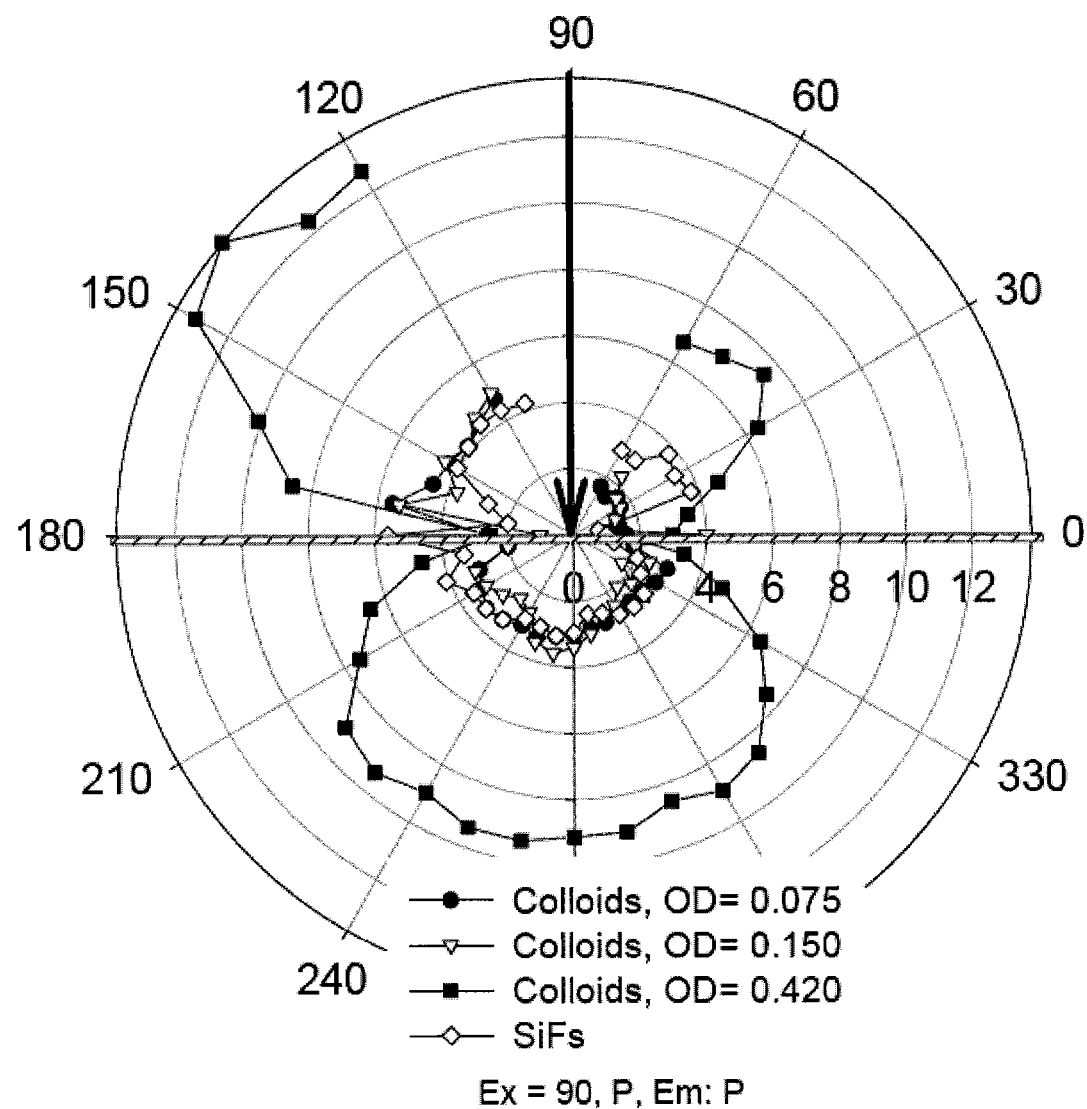
FIG. 9 shows the fluorescence enhancement factor for colloid coated glass as a function of surface loading (optical density measurements). The enhancement factor was calculated as the ratio of the fluorescein fluorescence intensity on silver/intensity on glass. The enhancement factor for traditional silver island films (SiFs) is also shown.
Figure 10:
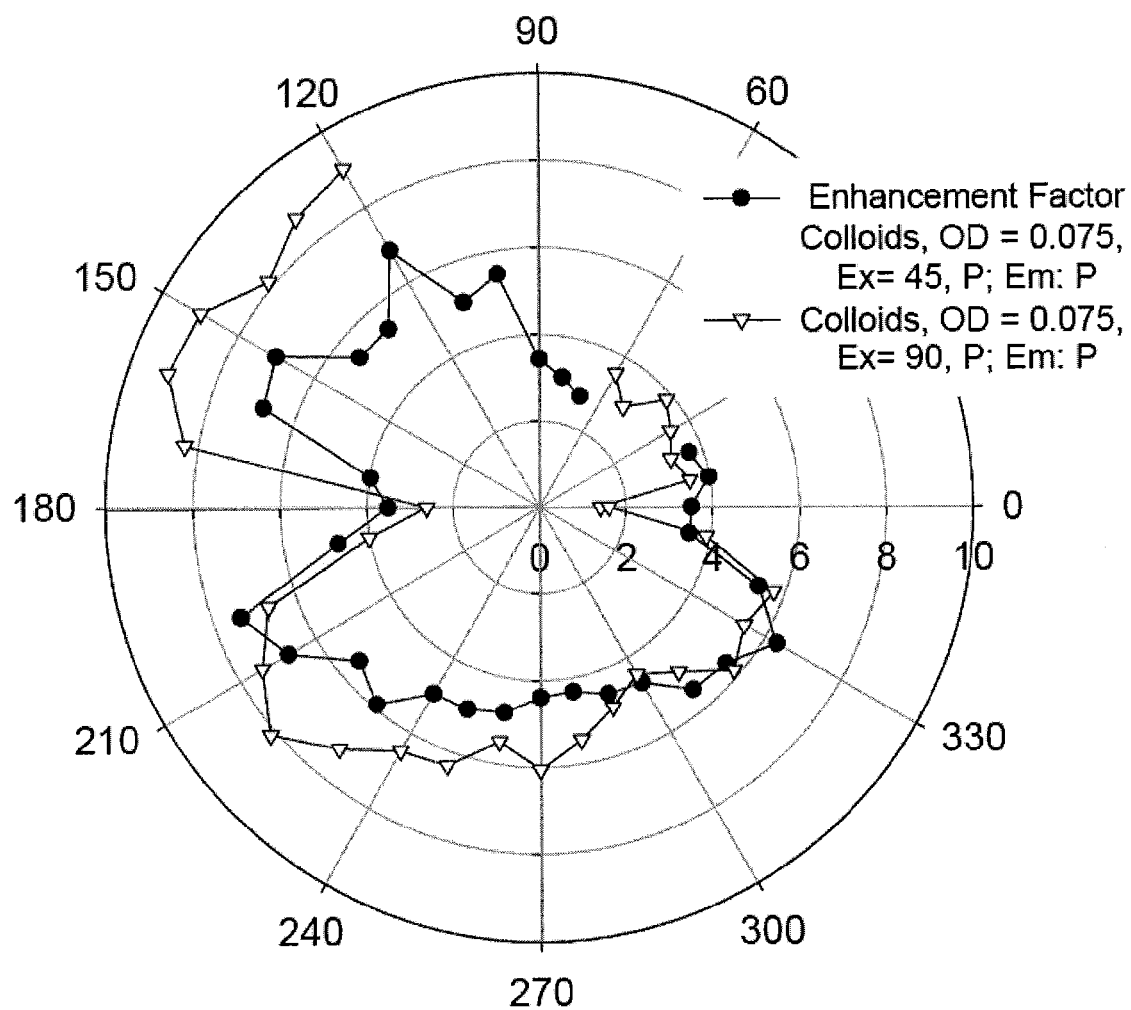
FIG. 10 shows the enhancement factor for FITC-HSA coated silver colloids deposited onto glass slides with excitation at both 45 and 90 degrees. The excitation and emission collected was p-polarized. Surface colloid OD=0.075.

FIG. 9 shows that as the optical density increases, the enhancement factor increases, wherein the enhancement factor is the ratio of fluorescein fluorescence intensity on silver: intensity on glass. Further, it is evident from FIG. 10 that the incident angle of excitation affects the enhancement factor and that 90 degrees incident angle increases the enhancement factor especially at detection angles 120 degrees and 220 degrees.

Figure 11:
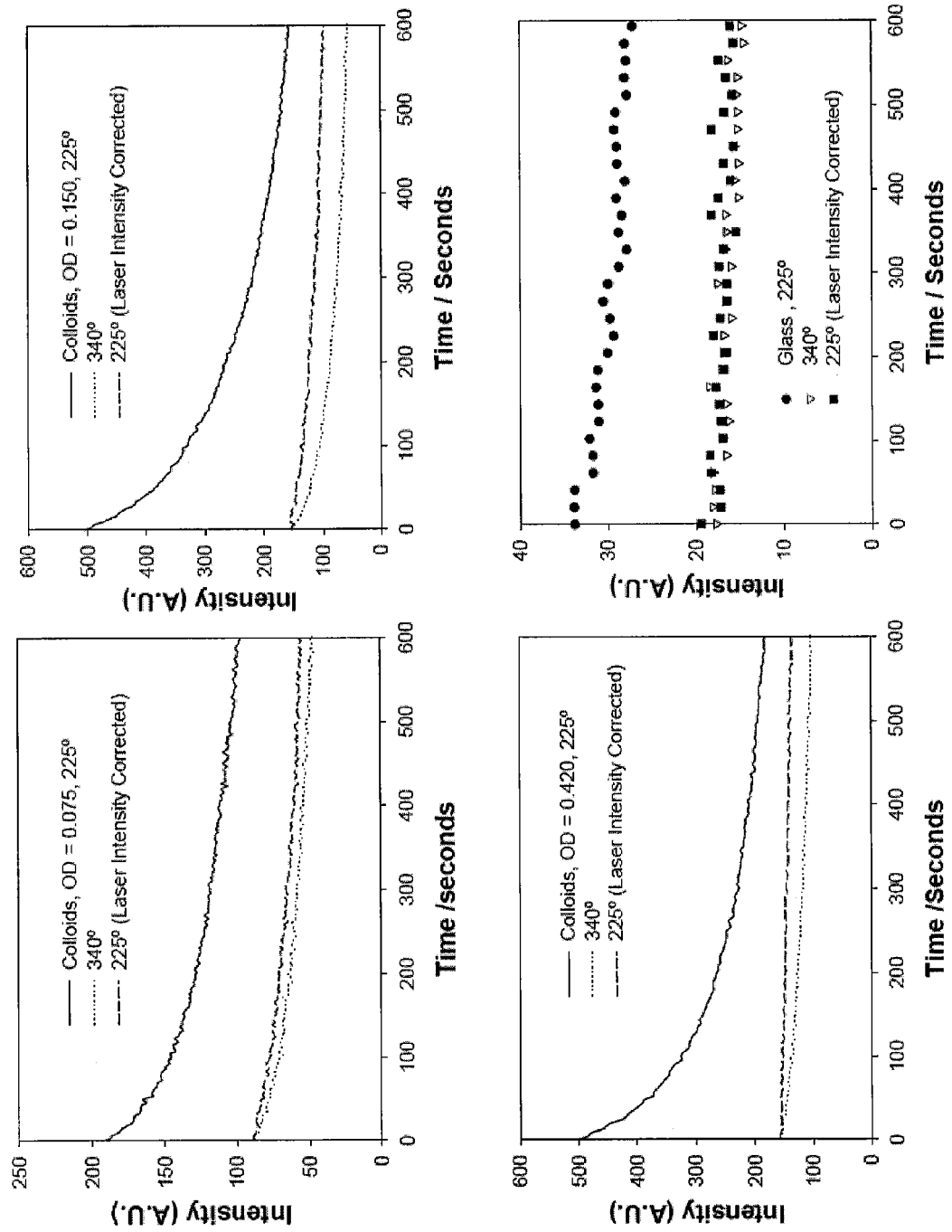
FIG. 11 shows the FITC-HSA angular emission intensity (photostability) as a function of time with 470 nm excitation at 90 degrees, for colloid coated surfaces of different optical density, and also on glass.

FIG. 11 shows that the intensity, related to the photostability, maintains an increasingly consistent emission as the optical density increases and is more stable at detection at 340 degrees. However, at the detection angle of 340 degrees, the intensity is reduced relative to the emission signal detected at 225 degrees.

Figure 12:
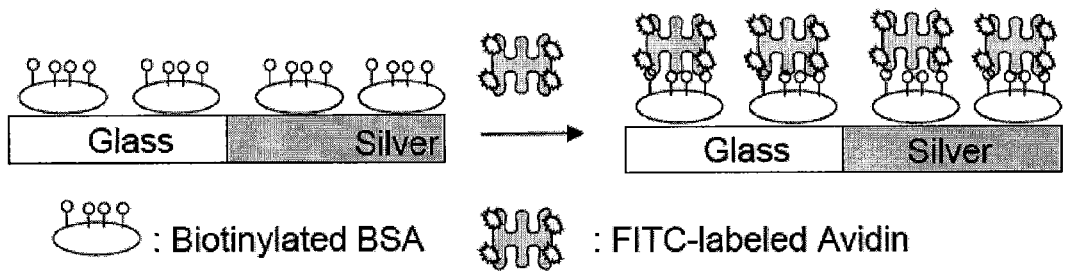
FIG. 12 shows a model assay system using angular-dependent metal-enhanced fluorescence (Top), and the angular emission spectra as a function of additions of Avidin-FITC (225 Degrees—Middle) and (340 degrees—Bottom).
Figure 12:
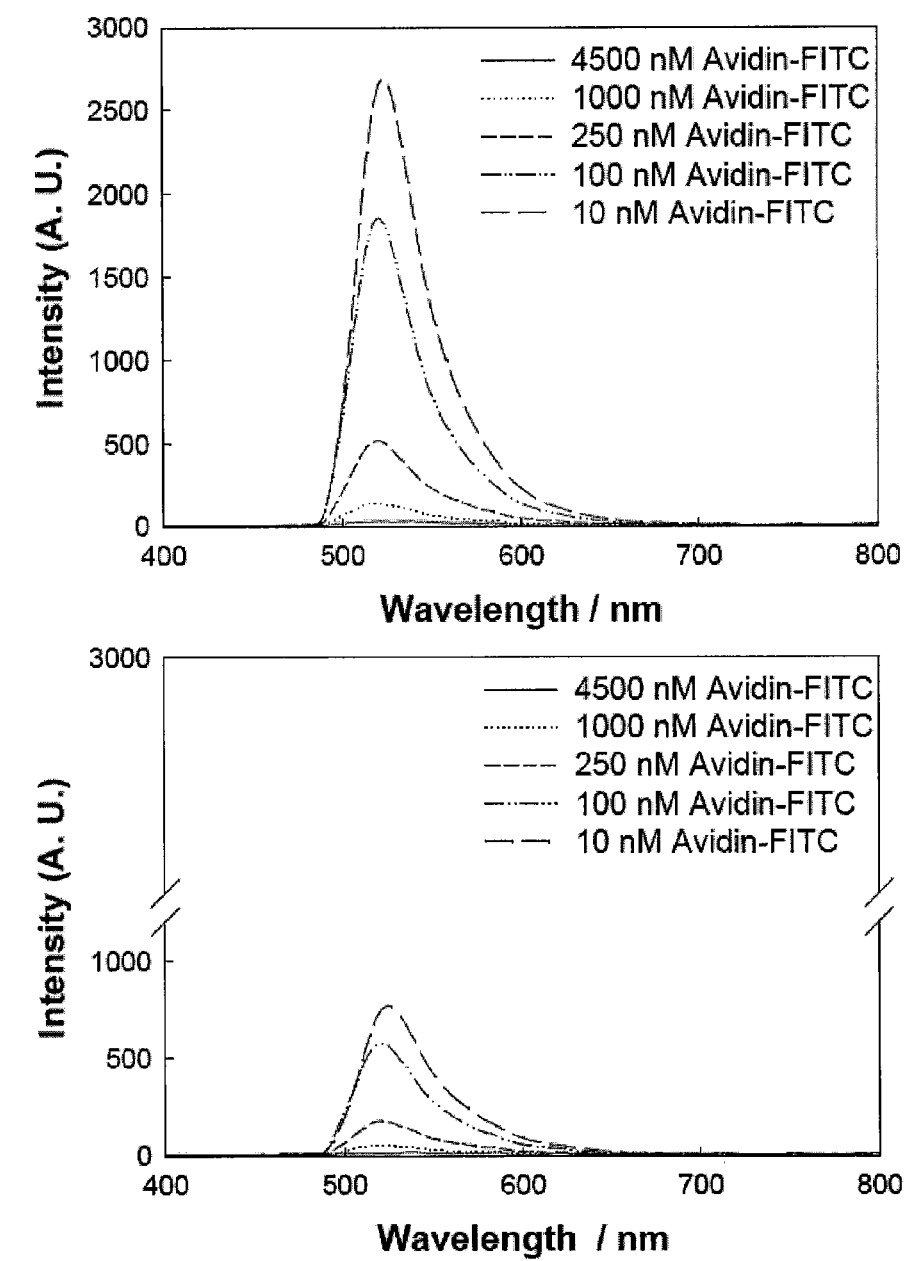

FIG. 12 illustrates the model assay described herein that is based on the well-known interactions of biotin and avidin. Biotin groups are introduced to the surface through biotinylated-BSA, which readily forms a monolayer on the surfaces of glass and SiFs. Binding the biotinylated-BSA to the SiFs and the glass was accomplished by incubating 10 µM biotinylated-BSA solution in the "black-body" micro cuvettes for 1 hour, followed by rinsing with water to remove the unbound material. For the model assay, then 30 µl of 1 µM FITC-labeled avidin was subsequently added into the biotinylated-BSA coated glass and SiFs coated micro cuvettes. 470 nm laser line excitation for 1 minute was used before the emission intensity and fluorescence spectra was taken at different angles, that being at 225 degrees and 340 degrees.

Fluorescence measurements on SiFs were performed by placing the films on a stationary stage equipped with a fiber-optic mount on a 15-cm-long arm (normal to sample). The output of the fiber was connected to an Ocean Optics HD2000 spectrofluorometer to measure the florescence emission spectra.

Figure 13:
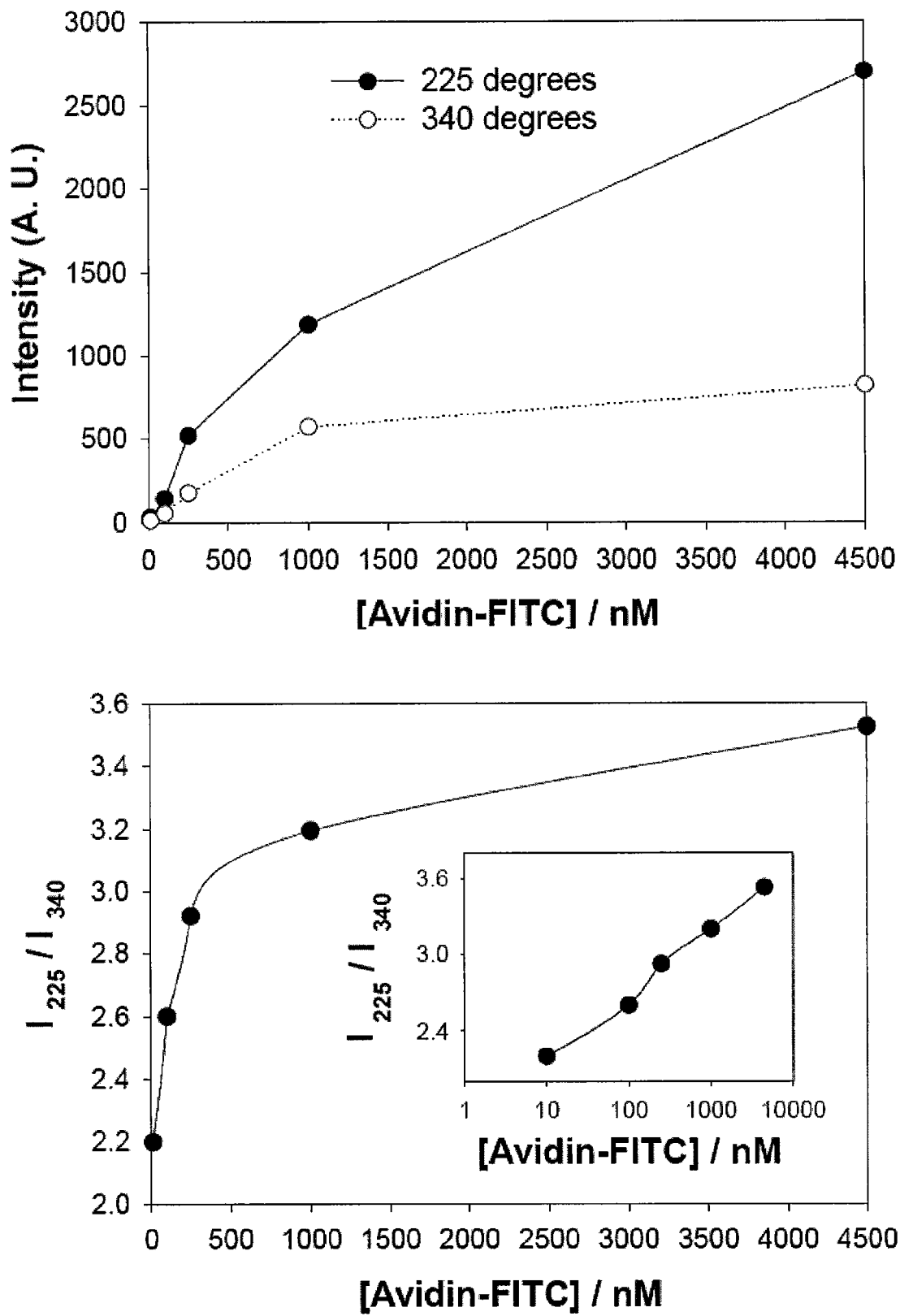
FIG. 13 shows the peak emission intensity at both 225 and 340 degrees as a function FITC-Avidin (Top), and an angular ratiometric plot Vs FITC-Avidin concentration (Bottom). Bottom Insert-Log FITC-Avidin concentration.

As shown in FIG. 13, the intensity of the emissions is increased at 225 degrees relative to the 340 degrees angular detection.

As shown above, silver colloids are very effective in showing that as surface of colloids increase there is an increased contribution of the scattering portion of the colloid's excitation spectrum. The combining of the emissions of the excited fluorophore and the metal colloid emits with the photophysical characteristics of the fluorophore after the excitation and the partial radiationless energy transfer between the excited states of the fluorophore and the surface plasmons of the silver colloids.

Notably, silvered surface perform very well in MEF application when stored in water and used within a few days after preparation. However, the silver surface do deteriorate after long storage time and are prone to oxidation at all temperatures. Thus, an alternative metal colloid, such as gold was tested to determine its applicability for detection using angular-dependent fluorescence emissions.

FITC-labeled human serum albumin (FITC-HSA) and premium quality APS-coated glass slides (75 mm×25 mm) were obtained from Sigma-Aldrich.

Gold colloids of 40 and 200 nm diameters were obtained from Ted Pella, Inc, CA. All chemicals were used as received. The deposition of the gold colloids onto APS-coated glass slides was achieved by incubating the glass slides in a freshly prepared solution of gold colloids overnight. The APS-coated glass slides were coated with gold colloids due to the affinity between gold and amine groups, similar to the binding of silver to the amine groups of the surface poly-lysine [7], as demonstrated previously. The colloids are positioned on the surface substrate, that being either glass or a plastic surface, in either a random or preferably a homogeneous arrangement such as shown in FIG. 1. The other half of the glass slides were left intentionally blank and served as the control experiments. The gold colloid deposited glass slides were rinsed with deionized water several times prior to the fluorescence experiments.

All absorption measurements were performed using a Varian Cary 50 UV-Vis spectrophotometer.

Binding the FITC-HSA to the gold colloids and to the glass surfaces was accomplished by incubating a 35 µl solution of 10 µM FITC-HSA on gold colloids and on glass for 30 min, followed by rinsing with PBS buffer to remove the unbound material. Both the gold colloids and glass surfaces were coated with the FITC-HSA, which is known to passively absorb to noble metal surfaces and form a ≈4 nm thick protein monolayer, allowing the study of the fluorescence spectral properties of non-covalent FITC-HSA complexes in the absence and presence of gold colloids. By equally coating the surfaces with FITC-HSA the enhancement factor (benefit) obtained from using the gold could be determined, i.e. Intensity on gold/Intensity on glass, given that both surfaces are known to have an ≈equal monolayer coverage.

Figure 18:
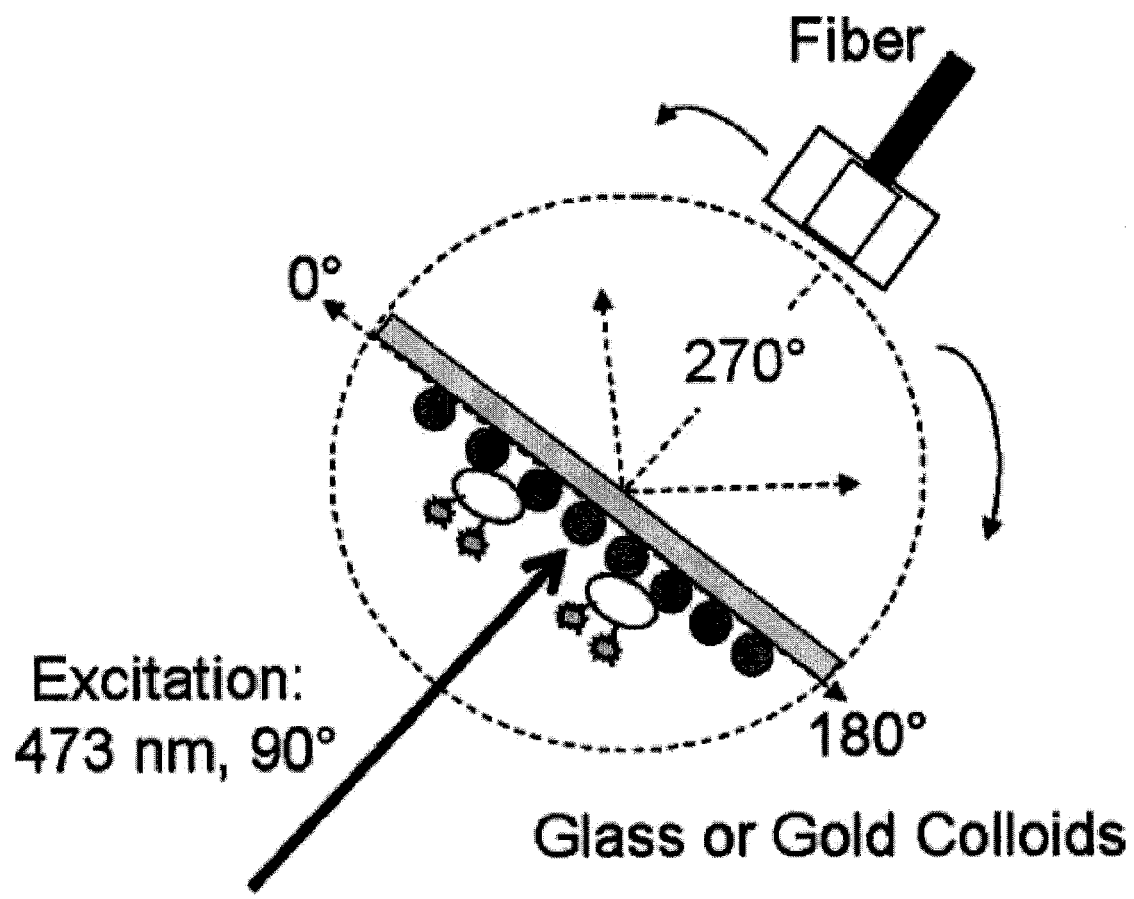
FIG. 18 shows the experimental setup (Top), Definition of "p" and "s" polarized light: p- and s- polarized light has the electric field polarized parallel and perpendicular to the plane of incidence, respectively.
Figure 18:
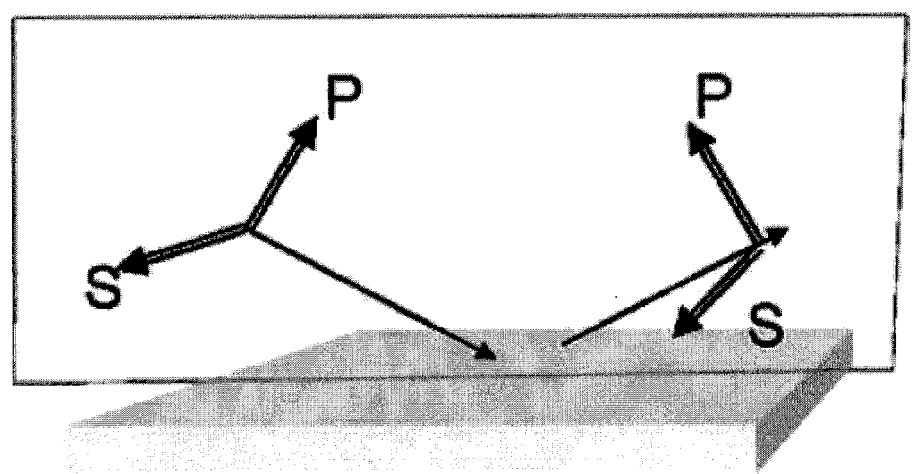

Angular-dependent fluorescence spectra of FITC-HSA on glass and gold colloids were collected using an X-Y rotating stage (Edmund Optics), that was modified to hold a glass slide, with a fiber optic mount (FIG. 18-Top). The FITC-HSA on glass and gold colloids was excited with a polarized laser source, the second harmonic (473 nm) of the diode-pumped Nd:YVO4 laser (compact laser pointer design, output power ≈30 mW), at an angle of 90 degrees, and a neutral density filter was used to adjust the laser intensity. The excitation light was eliminated with an emission filter at 488 nm. The angular-dependent fluorescence emission peak of FITC-HSA and FITC-avidin through a polarizer were recorded at 517 nm using an Ocean Optics HD2000 spectrofluorometer. The emission intensity at the angles between 70 and 110° were not collected since the holder for the fiber optic assembly obstructed the view at those angles.

The real-color photographs of FITC-HSA on gold colloids and glass slides were taken with a Canon digital camera (SI-IS, 3.2 Mega Pixel, 10× optical zoom) using the same long-pass filter that was used for the emission spectra.

Figure 19:
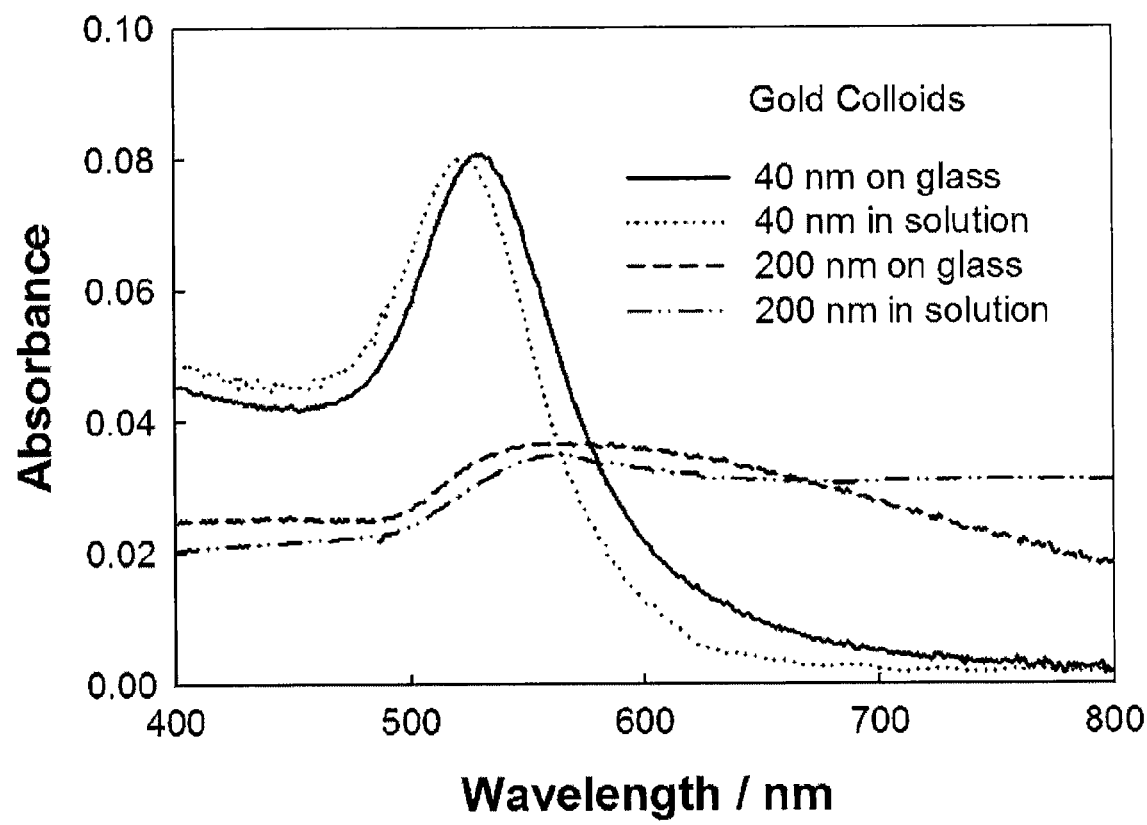
FIG. 19 shows the absorption spectra of gold colloids in solution and gold colloids deposited onto glass slides.

87 FIG. 19 shows the absorption spectra of 40 and 200 nm gold colloids deposited on to glass substrates and in solution. The absorption spectrum for both 40 and 200 nm gold colloids deposited onto glass slides were similar to those in solution, indicative of a homogeneous deposition of gold colloids. The surface plasmon resonance (SPR) peak of 40 nm gold colloids showed a slight red shift from 525 nm in solution to 530 nm on the glass, where only minimal change in the SPR peak of 200 nm gold colloids was observed.

The homogeneous deposition of gold colloids, as achieved here, is important in the view of producing reproducible surfaces for the evaluation of the potential of gold colloids for MEF-based assays. It was previously shown that aggregated metal colloids deposited on planar surfaces provide better fluorescence enhancements [9-14], which is due to the increased electric field contribution from between the aggregated metal colloids. However, these surfaces lack the reproducibility necessary for the verification of MEF from gold colloids. Thus, for this experiment, the gold colloids were deposited in a homogenous fashion.

Figure 20:
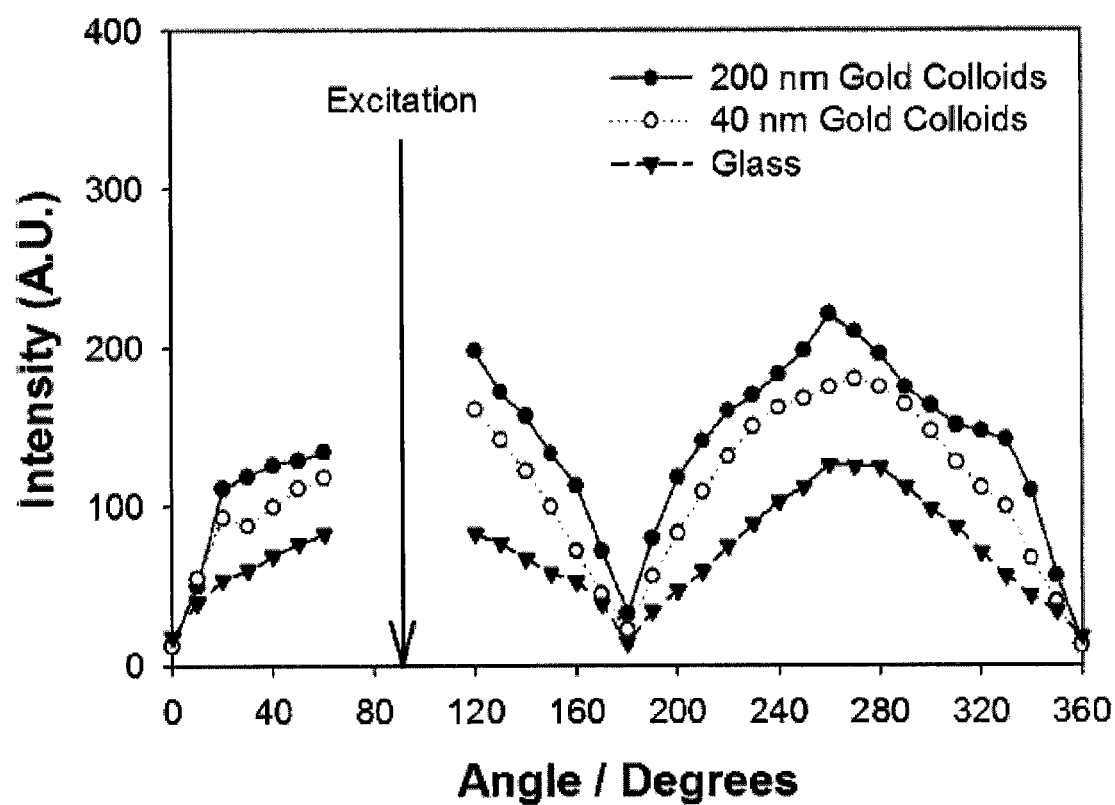
FIG. 20 shows the angular dependent p-polarized fluorescence emission intensity (measured at 517 nm) for FITC-HSA on glass and gold colloids. Excitation was p-polarized and was at an angle of 90 degrees.

FIG. 20 shows the p-polarized emission intensity of FITC-HSA on glass substrates and on 40 and 200 nm gold colloids measured at 517 nm in an angular dependent fashion, i.e. over 360 degrees, where the excitation source was positioned perpendicular to the glass substrate, on the same side as the gold colloids and the fluorophores, c.f. FIG. 18. The emission intensities between the angles of 70 and 110° were not collected due to the obstruction by the fiber optic holder as explained in the Experimental section. The emission intensity of FITC-HSA on glass and gold colloids was the lowest at the angles of 0 degrees (equivalent to 360 degrees) and 180 degrees, and was the highest at 270 degrees (at the back of the glass substrates). The emission intensity at all angles was higher on 200 nm gold colloids than 40 nm gold colloids and glass, and the emission intensity at all angles was higher on 40 nm gold colloids than glass. That is, with respect to the emission intensity of FITC-HSA on glass, the emission intensity on 40 and 200 nm gold colloids were enhanced 1.75 and 2.5 times, respectively.

Figure 21:
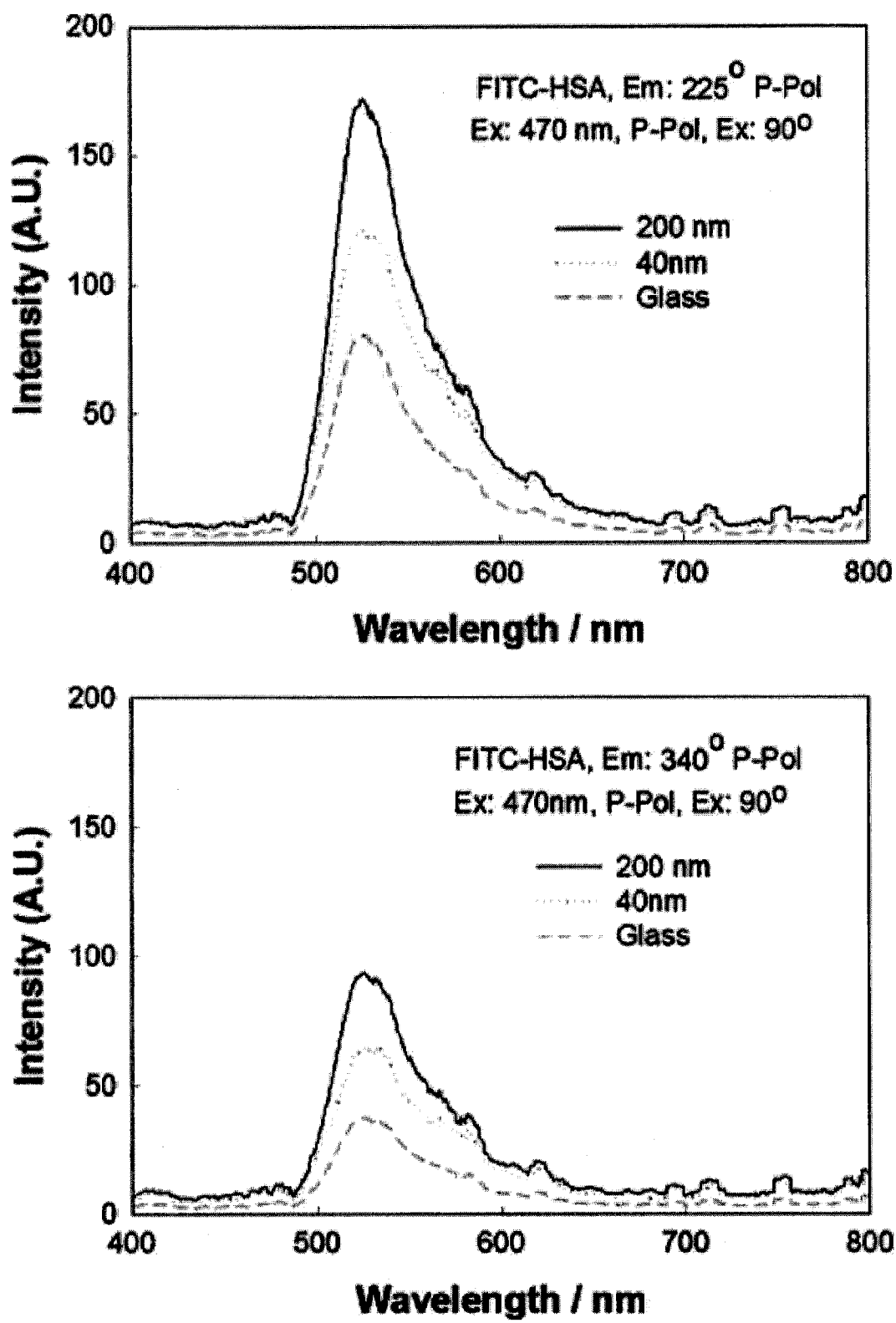
FIG. 21 shows P-Polarized emission spectra of FITC-HAS on glass and gold colloids observed at 225 degrees (Top) and at 340 degrees (Bottom). Excitation source was p-polarized and was positioned at an angle of 90 degrees. (A.U. arbitrary units).

FIG. 21 shows the p-polarized emission spectra of FITC-HSA on glass and gold colloids observed at 225 degrees and at 340 degrees. The emission spectra shown here are typical of those of FITC measured on glass substrates [3], and have a maximum emission peak of 517 nm. As also shown in FIG. 21, the emission intensity at 517 nm is the highest for 200 nm gold colloids as compared to 40 nm gold colloids and glass, and the emission intensity is indeed higher for 40 nm gold colloids than FITC-HSA coated glass.

Figure 22:
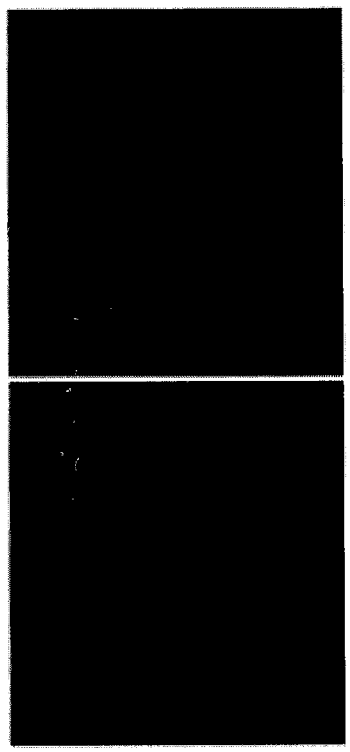
FIG. 22 shows photographs of fluorescence emission of FITC-HAS on glass and 200 nm gold colloids taken through an emission filter (488 nm) at 225 and 340 degrees.
Figure 22:
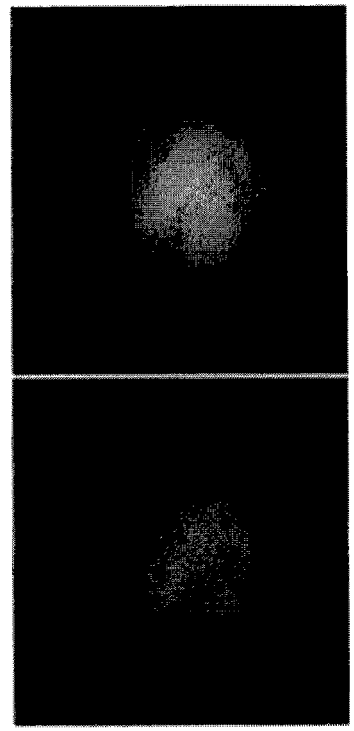
Figure 23:
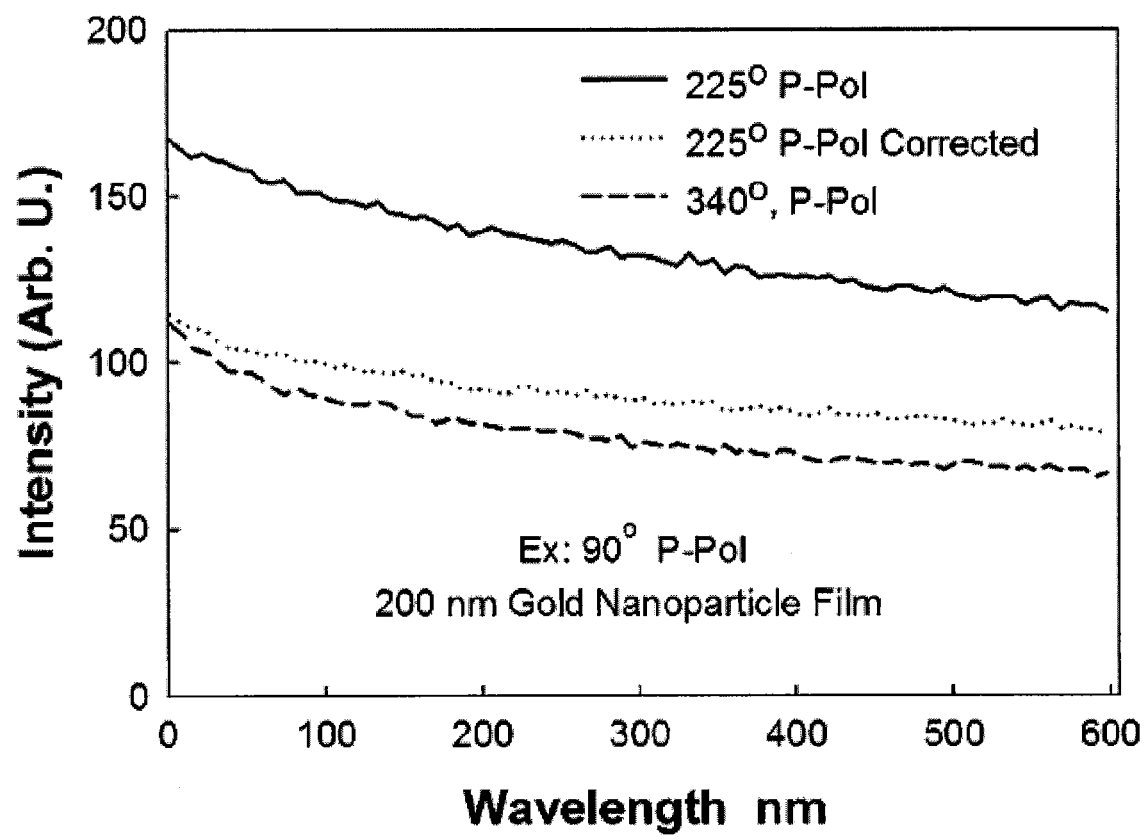
FIG. 23 shows the photostability of FITC-HSA from 200 nm gold colloids. Emission intensity (p-polarized) was measured at 517 nm and collected at 225 and 340 degrees.

A visual proof for the enhancement of fluorescence emission of FITC-HSA on gold colloids with respect to that of on glass is provided in FIG. 22, where the real-color photographs of fluorescence emission on glass and on 200 nm gold colloids taken at an angle of 225 and 340 degrees through an emission filter are shown. The fluorescence emissions on 200 nm gold colloids at both angles are much brighter than that of the glass substrate. FIG. 22 also shows that the emission intensity of FITC-HSA on both glass and 200 nm gold colloids is higher when measured at 225 degrees than that of measured at 340 degrees.

Figure 17:
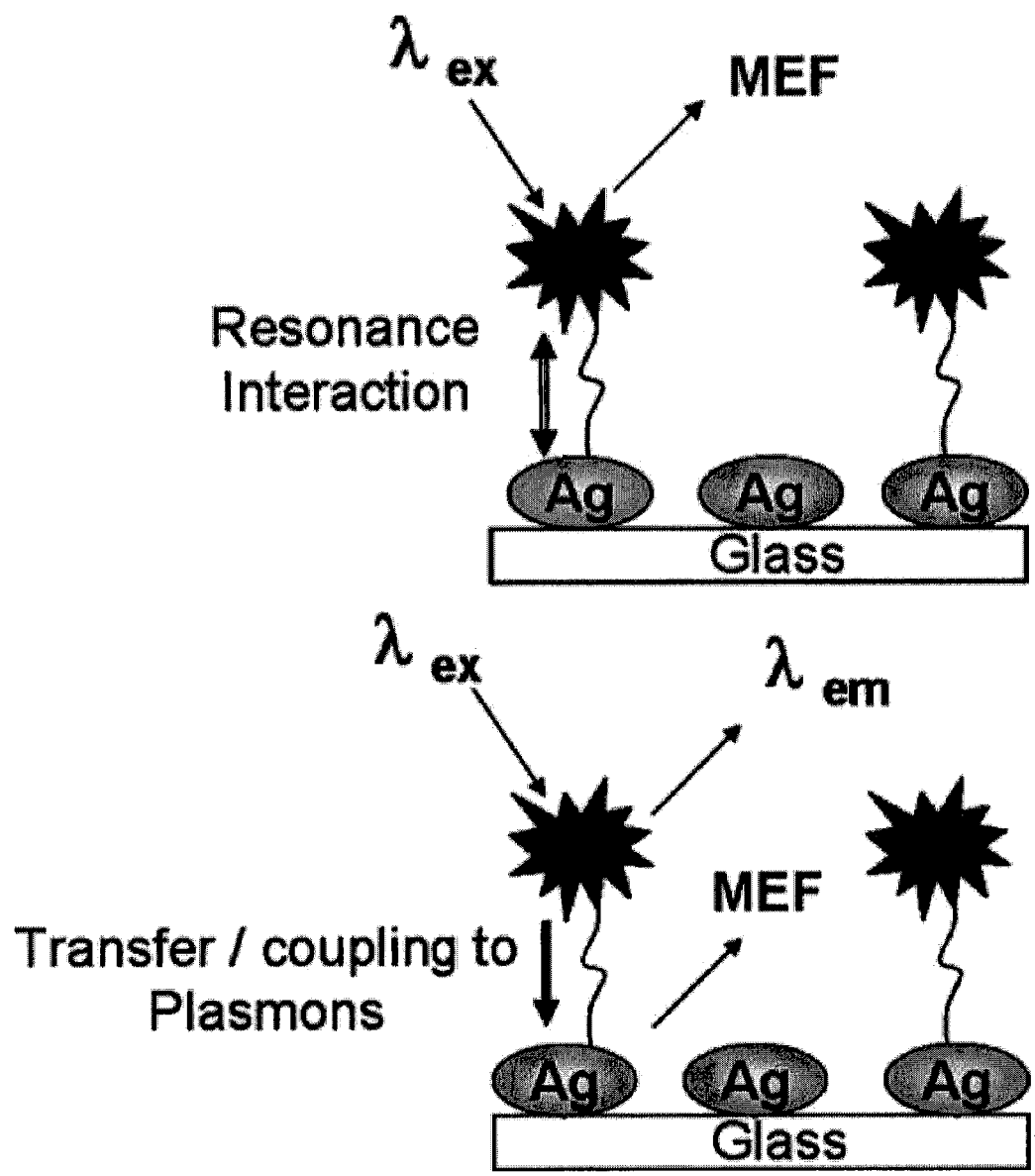
FIG. 17 shows the graphical representation of the original interpretation of Metal Enhanced Fluorescence (Top) and the current interpretation which is plasmon-assisted (bottom). Both Ag and Au surface can be used.

It is well established that the emission of fluorophores positioned in close proximity to gold colloids up to 30 nm in diameter [17-19] is "quenched," due to the non-radiative energy transfer from the excited states of the fluorophores to the gold colloids. This energy is most probably then dissipated as heat. Since gold colloids less than 30 nm diameter result in quenching, and the larger gold colloids (larger than 40 nm) have increased forward scattering [22], and an increased scattering component in their extinction spectrum, then the gold colloids with a diameter of 40 nm and larger were predicted to enhance the fluorescence emission of fluorophores within close proximity. This hypothesis has been demonstrated with the data for both 40 and 200 nm gold colloids and FITC-HSA, c.f. FIGS. 21 and 22. The use of fluorophores conjugated to a protein here, places the fluorophores within 4 nm of the gold colloid-coated surface. In this regard, gold colloid surface plasmons are excited in a non-radiative fashion [17, 18], which then efficiently scatter light, i.e., the photophysical properties of the fluorophore, c.f. FIG. 17-*bottom*.

In many examples of fluorescence based sensing, it is fluorophore detectability that governs the utility and sensitivity of the sensing approach [28]. In general, the detectability of a fluorophore is determined by two factors: the extent of background emission from the sample and the photostability of the fluorophore. A highly photostable fluorophore, such as tetramethyl rhodamine [28] can undergo about $10^6$ excitation-relaxation cycles prior to photobleaching. While this can yield as many as $10^4$ detectable photons per fluorophore it should be realized that the vast majority of fluorophores photodegrade after far fewer excitation-emission event cycles. Subsequently, the photostability of FITC-HSA on the 200 nm gold colloids was tested at two different angles, 225 and 340 degrees. The relative intensities of the plots reflect that more detectable photons can be observed per unit time from the 200 nm gold colloids at 225 degrees, as compared 340 degrees, where the integrated areas under the plots is proportional to the photon flux from the respective samples.

These results indicate that gold colloid-coated surfaces can be used in fluorescence-based applications, such as in assays, where the fluorescence emission is enhanced and fluorophores became more photostable. Thus, the gold colloids are likely to find common place in MEF as they are less prone to oxidation, as compared to silver colloids, and the fact that more surface chemistries have been developed for gold surfaces.

Although the invention has been described with respect to specific embodiments, the details are not to be construed as limitations, for it will become apparent that various embodiments, changes and modifications may be resorted to without departing from the spirit and scope thereof, and it is understood that such equivalent embodiments are intended to be included within the scope of this invention.

References

All the contents of all references cited herein are hereby incorporated by reference herein for all purposes.

1. Aslan K, Gryczynski I, Malicka J, Lakowicz J R, Geddes C D (2005) Metal-enhanced fluorescence: An emerging tool in biotechnology. *Curr Opin Biotechnol* 16(1):55-62.
2. Aslan K, Gryczynski I, Malicka J, Lakowicz J R, Geddes C D (2005) In: Shayne G (ed) Drug discovery handbook. Wiley, New Jersey, pp 603-666.
3. Aslan K, Holley P, Geddes C D (2006) Microwave-accelerated metal enhanced fluorescence (MAMEF) with silver colloids in 96-well plates: Application to ultra fast and sensitive immunoassays, High Throughput Screening and drug discovery. *J Immunol Methods* 312:137-147.
4. Geddes C D, Aslan K, Gryczynski I, Malicka J, Lakowicz J R (2004) In: Geddes C D, Lakowicz J R (eds) Reviews in Fluorescence 2004. Kluwer Academic/Plenum Publishers, New York, pp 365-401.
5. Aslan K, Geddes C D (2006) Microwave accelerated and metal enhanced fluorescence myoglobin detection on silvered surfaces: Potential application to myocardial infarction diagnosis. *Plasmonics* 1(1):53-59.
6. Geddes C D, Aslan K, Gryczynski I, Malicka J, Lakowicz J R (2005) Radiative decay engineering. In: Geddes C D, Lakowicz J R (eds) Topics in fluorescence spectroscopy. Kluwer Academic/Plenum Publishers, New York, pp 401-448.
7. Malicka J, Gryczynski I, Geddes C D, Lakowicz J R (2003) Metal-enhanced emission from indocyanine green: A new approach to in vivo imaging. *J Biomed Opt* 8(3):472-478.
8. Geddes C D, Cao H, Gryczynski I, Grcyzynski Z, Fang J, Lakowicz J R (2003) Metal-enhanced fluorescence (MEF) due to silver colloids on a planar surface: Potential applications of indocyanine green to in vivo imaging. *J Phys Chem A* 107(18):3443-3449.
9. Aslan K, Leonenko Z, Lakowicz J R, Geddes C D (2005) Fast and slow deposition of silver nanorods on planar surfaces: Application to metal-enhanced fluorescence. *J Phys Chem B* 107(13):6247-6251.
10. Aslan K, Leonenko Z, Lakowicz J R, Geddes C D (2005) Rapid deposition of triangular silver nanoplates on planar surfaces: Application to metal-enhanced fluorescence. *J Phys Chem B* 109(8):3157-3162.
11. Parfenov A, Gryczynski I, Malicka J, Geddes C D, Lakowicz J R (2003) Enhanced fluorescence from fluorophores on fractal silver surfaces. *J Phys Chem B* 107:8829-8833.
12. Parfenov A, Geddes C D, Lakowicz J R (2003) Photodeposition of silver can result in metal-enhanced fluorescence. *Appl Spectrosc* 57(5):526-531.
13. Geddes C D, Parfenov A, Roll D, Fang J, Lakowicz J R (2003) Electrochemical and laser deposition of silver for use in metal-enhanced fluorescence. *Langmuir* 19(15):6236-6241.
14. Aslan K, Badugu R, Geddes C D (2005) Metal-enhanced fluorescence from plastic substrates. *J Fluoresc* 15(2):99-104.
15. Geddes C D, Parfenov A, Roll D, Gryczynski I, Malicka J, Lakowicz J R (2004) *Spectrochimica Acta Part A* 60(8-9):1977-1983.
16. Aslan K, Leonenko Z, Lakowicz J R, Geddes C D (2005) Annealed silver-island films for applications in metal-enhanced fluorescence: Interpretation in terms of radiating plasmons. *J Fluoresc* 15(5):643-654.
17. Aslan K, Perez-Luna V H (2004) Quenched emission of fluorescence by ligand functionalized gold nanoparticles. *J Fluoresc* 14:401-405.
18. Dulkeith E, Morteani A C, Niedereichholz T, Klar T A, Feldmann J, Levi S A, van Veggel F C J M, Reinhoudt D N, Moller M, Gittins D I (2002) Fluorescence quenching of dye molecules near gold nanoparticles: Radiative and non-radiative effects. *Phys Rev Lett* 89:203002.
19. Dulkeith E, Ringler M, Klar T A, Feldmann J, Javier A M, Parak W J (2005) Gold nanoparticles quench fluorescence by phase induced radiative rate suppression. *Nano Lett* 5(4):585-589.
20. Yguerabide J, Yguerabide E (1998) Light-scattering submicroscopic particles as highly fluorescent analogs and their use as tracer labels in clinical and biological applications—I. *Theor Anal Biochem* 262:137-156.
21. Yguerabide J, Yguerabide E (1998) Light-scattering submicroscopic particles as highly fluorescent analogs and their use as tracer labels in clinical and biological applications—II. Experimental characterization. *Anal Biochem* 262:157-176.
22. Asian K, Holley P, Davies L, Lakowicz J R, Geddes C D (2005) Angular-ratiometric plasmon-resonance based light scattering for bioaffinity sensing. *J Am Chem Soc* 127:12115-12121.
23. Mie G (1908) *Ann Phys* 25:377-445.

24. Lakowicz J R (2001) Radiative decay engineering: biophysical and biomedical applications. *Anal Biochem* 298; 1-24.
25. Lakowicz J R (2005) Radiative decay engineering 5: Metal-enhanced fluorescence and plasmon emission. *Anal Biochem* 337:171-194.
26. Liebermann T, Knoll W (2000) Surface-plasmon field-enhanced fluorescence spectroscopy colloids and surfaces. A: *Physicochemical and Eng Aspects* 171:115-130.
27. Lakowicz J R (2004) Radiative decay engineering 3. Surface plasmon-coupled directional emission. *Anal Biochem* 324:153-169.
28. Lakowicz J R (1999) Principles of fluorescence spectroscopy. Kluwer, New York.

That which is claimed is:

1. A method for detecting emissions from fluorescent molecules positioned near metallic structures, the method comprising:
   (a) positioning the fluorescent molecules near the metallic structures immobilized on a surface, wherein the surface comprises a multiplicity of metallic structures and wherein the fluorescent molecules are positioned from about 5 nm to about 30 nm from the metallic structures;
   (b) irradiating the fluorescent molecules with polarized radiation and at an excitation incidence angle in an amount sufficient to cause non-radiative transfer of energy from the fluorescent molecules to plasmons on the metallic structures; and
   (c) detecting angular plasmonic emissions from the metallic structures in combination with scattered emissions from the fluorescent molecules, at a detection angle different from that of the excitation incidence angle and wherein the detection angle is about 180 degrees relative to the angle of incidence.

2. A method for detecting emissions from fluorescent molecules positioned near metallic structures the method comprising:
   (i) positioning the fluorescent molecules near the metallic structures immobilized on a surface, wherein the surface comprises a multiplicity of metallic structures wherein the fluorescent molecules are positioned from about 5 nm to about 30 nm from the metallic structures;
   (ii) irradiating the fluorescent molecules with polarized radiation and at an excitation incidence angle in an amount sufficient to cause non-radiative transfer of energy from the fluorescent molecules to plasmons on the metallic structures; and
   (iii) detecting angular plasmonic emissions from the metallic structures in combination with scattered emissions from the fluorescent molecules, at a detection angle different from that of the excitation incidence angle, wherein the method for detecting emissions measures the concentration of an analyte, the method comprising:
   (a) preparing metallic structures positioned on the surface, wherein the metallic structures comprise a noble metal and at least partially coated with a binding component having an affinity for the analyte;
   (b) contacting the binding components with the analyte that has an affinity for the binding component;
   (c) contacting any bound analyte with the fluorescence molecules;
   (d) exposing the system comprising the metallic structures and fluorescence molecules with excitation electromagnetic energy in an amount sufficient to excite the fluorescence molecules and surface plasmons, wherein the electromagnetic energy is delivered at an incident angle and at a frequency matching plasmon absorption maxima of the metallic structures; and
   (e) detecting the emission from surface plasmons and fluorescence molecules at a detection angle different from the incident angle, wherein the detection angle has been predetermined for the metallic structures and in a range from about 135 degrees to about 225 degrees relative to the angle of incidence.

3. A system of detecting angular-dependent metal enhanced fluorescence, the system comprising:
   metallic colloids positioned on a surface or in solution, wherein the metallic colloids are communicatively connected to a fluorophore tag, and wherein the fluorescent tag is positioned from about 5 nm to about 30 nm from the metallic colloids, wherein the metallic colloids are in an amount to provide an optical density from about 0.075 to 0.425 at a given wavelength thereby increasing emissions from the fluorophore tag and plasmonic emissions from the metallic colloids;
   a source of electromagnetic energy positioned to radiate at least the fluorophore tag at an excitation angle; and
   a detector positioned at a detection angle for measuring the radiation emissions from the metallic colloids coupled with emission from the fluorophore tag.

4. The system according to claim 3, wherein the metallic colloid is silver or gold.

5. The system according to claim 3, wherein the surface is a glass or plastic substrate.

6. The system according to claim 3, wherein the excitation angle is perpendicular to the detection angle.

7. The system according to claim 3, wherein the emissions increase as the size of the colloid increases.

8. The system according to claim 3, wherein the colloid is from about 40 nm to 200 nm diameter.

9. The system according to claim 3, wherein a multiplicity of colloids are homogeneously positioned on the surface.

* * * * *